US012778463B2

(12) United States Patent
Mäntele et al.

(10) Patent No.: US 12,778,463 B2
(45) Date of Patent: Nov. 3, 2026

(54) METHOD AND APPARATUS FOR ANALYTE MEASUREMENT INCLUDING REAL-TIME QUALITY ASSESSMENT AND IMPROVEMENT

(71) Applicant: DiaMonTech AG, Berlin (DE)

(72) Inventors: Werner Mäntele, Kiefersfelden-Mühlbach (DE); Thorsten Lubinski, Berlin (DE); Sergius Janik, Berlin (DE); Michael Kaluza, Berlin (DE)

(73) Assignee: DiaMonTech AG, Berlin (DE)

(*) Notice: Subject to any disclaimer, the term of this patent is extended or adjusted under 35 U.S.C. 154(b) by 828 days.

(21) Appl. No.: 17/926,084

(22) PCT Filed: May 20, 2021

(86) PCT No.: PCT/EP2021/063521
§ 371 (c)(1),
(2) Date: Nov. 17, 2022

(87) PCT Pub. No.: WO2021/234113
PCT Pub. Date: Nov. 25, 2021

(65) Prior Publication Data

US 2023/0181063 A1 Jun. 15, 2023

(30) Foreign Application Priority Data

May 20, 2020 (WO) ................. PCT/EP2020/064153
Jul. 20, 2020 (WO) ................. PCT/EP2020/069629

(51) Int. Cl.
*A61B 5/1455* (2006.01)
*A61B 5/00* (2006.01)
(Continued)

(52) U.S. Cl.
CPC ........ *A61B 5/14532* (2013.01); *A61B 5/1075* (2013.01); *A61B 5/1172* (2013.01);
(Continued)

(58) Field of Classification Search
None
See application file for complete search history.

(56) References Cited

U.S. PATENT DOCUMENTS

| | | | |
|---|---|---|---|
| 7,729,734 | B2 | 6/2010 | Mandelis et al. |
| 11,946,887 | B2 | 4/2024 | Lubinski et al. |

(Continued)

FOREIGN PATENT DOCUMENTS

| | | | |
|---|---|---|---|
| EP | 1 048 265 | A1 | 11/2000 |
| EP | 2082214 | A1 | 7/2009 |

(Continued)

OTHER PUBLICATIONS

International Searching Authority/EP, International Search Report and Written Opinion of the International Searching Authority, Application No. PCT/EP2021/063521, dated Nov. 24, 2021, 30 pages.

(Continued)

*Primary Examiner* — Chu Chuan Liu
(74) *Attorney, Agent, or Firm* — Barclay Damon LLP

(57) ABSTRACT

A method of analyzing a material (12) comprising at least one analyte, wherein analyte-wavelength-specific measurements are interspersed with reference measurements (80), and wherein response signals obtained for the reference measurements (80) are used for one or more of calibrating an excitation radiation source (26) for generating said excitation radiation, calibrating said detection device, recognizing a variation in the measurement conditions by comparing results of individual reference measurements (80), adapting the analyte measurement procedure (78) with respect to one
(Continued)

or more of the entire duration thereof, the absolute or relative duration of analyte-wavelength-specific measurements for a given analyte-characteristic-wavelength, or terminating and/or restarting the analyte measurement procedure, and adapting the analysis carried out in the analyzing step.

16 Claims, 13 Drawing Sheets

(51) Int. Cl.

| | |
|---|---|
| ***A61B 5/107*** | (2006.01) |
| ***A61B 5/1172*** | (2016.01) |
| ***A61B 5/145*** | (2006.01) |
| ***A61B 5/1495*** | (2006.01) |

(52) U.S. Cl.
CPC ........ *A61B 5/1451* (2013.01); *A61B 5/14539* (2013.01); *A61B 5/14546* (2013.01); *A61B 5/1455* (2013.01); *A61B 5/1495* (2013.01); *A61B 5/443* (2013.01); *A61B 5/7221* (2013.01)

(56) References Cited

U.S. PATENT DOCUMENTS

| | | | | |
|---|---|---|---|---|
| 2013/0267799 | A1 | 10/2013 | Harjunmaa et al. | |
| 2018/0328835 | A1* | 11/2018 | Bauer .................. | A61B 5/1455 |
| 2018/0335381 | A1 | 11/2018 | Bauer et al. | |
| 2019/0302019 | A1 | 10/2019 | Bauer et al. | |

FOREIGN PATENT DOCUMENTS

| | | | |
|---|---|---|---|
| EP | 3650834 | A1 | 5/2020 |
| WO | 2019110597 | A2 | 6/2019 |
| WO | 2020094233 | A1 | 5/2020 |

OTHER PUBLICATIONS

Pleitez et al., "In Vivo Noninvasive Monitoring of Glucose Concentration in Human Epidermis by Mid-Infrared Pulsed Photoacoustic Spectroscopy," Analytical Chemistry, vol. 85, No. 2, Dec. 26, 2012, pp. 1013-1020, XP055499217, ISSN: 0003-2700, DOI: 10.1021/ac302841f.

Guo et al., "Noninvasive glucose detection in human skin using wavelength modulated differential laser photothermal radiometry," Biomedical Optics Express, vol. 3, No. 11, Nov. 1, 2012, 10 pages.

Chinese First Examination Opinion Notice cited in CN 202180060727.7 dated Jan. 31, 2026 with English Translation (28 pages).

* cited by examiner (continues on next page)

METHOD AND APPARATUS FOR ANALYTE MEASUREMENT INCLUDING REAL-TIME QUALITY ASSESSMENT AND IMPROVEMENT

CROSS-REFERENCE TO RELATED APPLICATIONS

This application is the national phase entry of International Patent Application No. PCT/EP2021/063521 filed on May 20, 2021, and claims the benefit of International Patent Application No. PCT/EP2020/064153 filed May 20, 2020, and International Patent Application No. PCT/EP2020/069629 filed Jul. 10, 2020, the disclosures of which are incorporated herein by reference in their entirety.

FIELD OF THE INVENTION

The present invention relates generally to methods and apparatus for analyzing a material as, for example, a fluid, comprising at least one analyte. In particular, the present invention relates to methods for non-invasive measurement of analytes in body fluids, such as glucose concentrations in human skin, in particular in the interstitial fluid of human skin.

BACKGROUND OF THE INVENTION

The present invention relates to a method of analyzing a material comprising at least one analyte. The method comprises a measurement procedure, in which the material is brought in thermal contact pressure transmitting contact with a measurement body, which thermal or pressure transmitting contact permits heat or pressure waves generated by absorption of excitation radiation in the material to be transferred to said measurement body. Excitation radiation is irradiated into the material to be absorbed therein, wherein the intensity of said excitation radiation is time-modulated, and wherein said excitation radiation comprises radiation of different analyte-characteristic-wavelengths that are irradiated one or both of simultaneously and sequentially.

Analyte-characteristic-wavelengths as understood herein are wavelengths that allow for determining the presence of an analyte by wavelength-selective absorption, and hence form the basis of the analysis. As such, analyte-characteristic-wavelengths may in particular include wavelengths corresponding to absorption maxima of the analyte. Further analyte-characteristic-wavelengths are wavelengths corresponding to local minima between two absorption peaks. Namely, the difference between a local absorption minimum and an adjacent peak is a good measure of the concentration of analyte in the material. Herein, the term "local minimum" indicates that the absorptivity of the analyte at the given wavelength is smaller than at nearby wavelengths, but is still appreciable, otherwise they would not be characteristic for the analyte. In particular, in preferred embodiments, the absorptivity at these local minima serving as analyte-characteristic wavelengths is more than 5%, preferably more than 10%, more preferably more than 20%, most preferably more than 30% of the highest absorption peak associated with any of the analyte-characteristic-wavelengths relied on in the analyte measurement. While wavelengths exactly corresponding with the absorption peaks or local absorption minima are the usually the preferred choices for the analyte-characteristic wavelengths, wavelengths close to the maxima/minima or between maxima and minima may also be used. Accordingly, as understood herein, "analyte-characteristic-wavelengths" are also wavelengths where the difference in absorption to that at the closest absorption peak or the closest local absorption minimum is less than 30%, preferably less than 20% of the difference in absorption between the closest absorption peak and closest local absorption minimum. Analyte-characteristic wavelengths may also include wavelengths where the absorption of other substances with which the analyte is mixed in the material, is particularly low.

Further, a physical response of the measurement body, or of a component included therein, to heat or pressure waves received from said material upon absorption of said excitation radiation is detected using a detection device which generates a response signal based on said detected physical response, said response signal being indicative of the degree of absorption of excitation radiation.

The present invention is not limited to any specific physical response to heat or pressure waves received from said material upon absorption of the excitation radiation, nor to any specific way of detecting this physical response in a manner that allows for generating a response signal that is indicative of the degree of absorption of excitation radiation. Various physical responses and corresponding detection methods have been previously proposed for these types of analyte measurement procedure by the present applicant and are briefly summarized below, and each of them may be applied in the present invention.

For example, the detection device may comprise a light source for generating a detection light beam travelling through at least a portion of said measurement body or a component included in said measurement body, and said physical response of the measurement body to heat or pressure waves received from said material upon absorption of said excitation radiation may be a local change in the refractive index of said measurement body or said component. In this case, the detection device may be configured for detecting one of a change in the light path or a change in the phase of detection light beam due to said change in refractive index of the material of the measurement body or the component included in the same.

For example, in various methods and devices described in detail in two earlier applications of the present applicant, published as WO 2015/193310 A1 and WO 2017/097824 A1, both of which included herein by reference, the measurement body is transparent for said detection light beam, and the detection light beam is directed to be totally or partially reflected at a surface of said measurement body that is in thermal contact with said material. In this case, the detection device may comprise a photodetector, in particular a position sensitive photodetector which is capable of detecting a degree of deflection, in particular a deflection angle of said detection light beam due to said local change in refractive index. Accordingly, in this case, the physical response to the heat or pressure waves received by the measurement body is a local change in refractive index, and the response signal is the detected degree of deflection which is indeed found to be indicative of the degree of absorption of the excitation radiation.

In alternative variants suggested by the present applicant, as for example disclosed in international application PCT/EP2019/064356, included herein by reference, said detection device may comprise an interferometric device allowing for assessing said change in phase of the detection beam and generating a response signal indicative of said change in phase. In this case, the physical response of the measurement body (or a component included therein) to heat or pressure waves received from said material upon absorption of said excitation radiation is again a local change in index of refraction, while the response signal is in this case an interferometric signal reflecting a change in the phase of the detection beam due to the local change in refractive index.

In yet alternative embodiments, the measurement body or a component in said measurement body may have electrical properties that change in response to a local change in temperature or a change in pressure associated therewith, and said detection device comprises electrodes for capturing electrical signals representing said electrical properties. Various possible setups are disclosed in WO 2019/110597 A2, included herein by reference. For example, the measurement body may comprise sections having piezoelectric properties, and pressure changes associated with received heat lead to electrical signals that can be recorded with the electrodes. In this case, the change in pressure resembles the physical response of the measurement body or of a component included therein, to heat received from the material upon absorption of the excitation radiation, which is detected using the piezoelectric properties of the measurement body and the electrode, and which leads to electrical signals representing the aforementioned response signal that is indicative of the degree of absorption of excitation radiation. In yet further variants, a temperature change due to received heat can be directly measured using very sensitive temperature sensors.

Note that in the following description, the physical response of the measurement body to heat received from the material is described in detail. However, it is to be understood that in various embodiments of the method and apparatus of the invention, the material is in pressure transmitting contact with the measurement body, and the physical response of the measurement body is a response to pressure waves received from the material. Herein, the expression "pressure transmitting contact" shall include all relations that allow the transfer of pressure waves from the material to the measurement body, and in particular, an acoustically coupled relation, where the coupling could be established by a gas, a liquid or a solid body. All detailed explanations given in connection with the thermal contact and physical response to heat received by the measurement body from the material shall be understood in combination with scenarios including pressure transmitting contact and physical response to pressure waves, where applicable, without explicit mention.

Note that the term "analyte" measurement procedure indicates that this measurement procedure is based on response signals obtained with excitation radiation at analyte-characteristic-wavelengths.

The method further comprises an analyzing step, in which said analyzing is carried out based, at least in part, on said response signal. Since in this case, the response signal is indicative of the degree of absorption of excitation radiation comprising "analyte-characteristic-wavelengths", the response signal is directly related to the concentration of the analyte in the material. Accordingly, the analyzing step is based at least in part on a measure of the concentration of the analyte in the material, and in some non-limiting applications, it may actually amount to determining this concentration.

For example, the above method has been employed by the applicant in devices for non-invasive measuring of a glucose level of a user. In this specific application, the "analyte" is formed by glucose, and the "material" is the skin of the user. It has been previously demonstrated that this method allows for very precise measurement of glucose concentration in the interstitial fluid within the skin of a person, which is found to be directly related with and hence representative of the glucose content of the patient's blood. Shown in FIG. 4 of the present application is the result of a Clark's error grid analysis taken from WO 2017/097824 A1, demonstrating that the above analysis method allows for predicting the actual glucose concentration of a person very precisely.

Nevertheless, it would be desirable to improve the accuracy of the analysis results even further, or to obtain the same accuracy of the analysis results in shorter time.

SUMMARY OF THE INVENTION

An object underlying the present invention is to provide a method and an apparatus of analyzing a material as set forth above that allow for improving the accuracy or reliability of the analysis results, reduce the period of time needed for the analysis, or both.

According to one aspect of the invention, this problem is solved in that during said analyte measurement procedure, a sequence of analyte-wavelength-specific measurements is carried out while maintaining said thermal or pressure transmitting contact between the material and the measurement body, wherein in each analyte-wavelength-specific measurement, excitation radiation with an analyte-characteristic-wavelength selected from a predetermined set of analyte-characteristic-wavelengths is irradiated and a corresponding response signal is obtained, and wherein at least some of said analyte-wavelength-specific measurements are interspersed with reference measurements, in which excitation radiation with a reference wavelength is irradiated and a corresponding response signal is obtained. Herein, said reference wavelength is a wavelength different from any of said analyte-characteristic-wavelengths. Preferably, the reference wavelength is a wavelength at which the absorption of said analyte is low, and in particular lower than 40%, preferably lower than 20% and most preferably lower than 10% of the highest absorption peak of the analyte associated with one of the analyte-characteristic-wavelengths.

Moreover, said response signals obtained for the reference measurements are used for one or more of

- calibrating an excitation radiation source for generating said excitation radiation, in particular the radiation intensity of said radiation source,
- calibrating said detection device, in particular the sensitivity of the detection device, recognizing a variation in the measurement conditions by comparing results of individual reference measurements,
- adapting the analyte measurement procedure with respect to one or more of the entire duration thereof, the absolute or relative duration of analyzing-wavelength-specific measurements for a given analyte-characteristic-wavelength, or terminating and/or restarting the analyte measurement procedure, and
- adapting the analysis carried out in the analyzing step.

The inventors have found that surprisingly, the accuracy of the analyte measurement procedure can be significantly improved if reference measurements are carried out during the course of the analyte measurement procedure. Herein, the analyte measuring procedure is a continuous measuring process in the sense that the thermal contact or pressure transmitting contact between the material and the measurement body is maintained throughout the measuring process. For example, if the material is formed by the fingertip of a person, this would mean that the fingertip is not lifted from the measurement body during the analyte measurement procedure. Moreover, during the analyte measurement procedure, a sequence of analyte-wavelength-specific measurements is carried out, wherein in each analyte-wavelength-specific measurement, excitation radiation with an analyte-characteristic-wavelength selected from a predetermined set of analyte-characteristic-wavelengths is irradiated and a corresponding response signal is obtained. This way, an absorption spectrum and eventually information regarding the concentration of the at least one analyte can be obtained.

However, according to this embodiment, at least some of said analyte-wavelength-specific measurements are interspersed with reference measurements, in which excitation radiation with a reference wavelength is irradiated into the material and a corresponding response signal is obtained. Herein, said reference wavelength is a wavelength different from any of the analyte-characteristic wavelengths. The reference wavelength may be a wavelength at which the absorption of said analyte is low and/or a wavelength at which the total absorption of the material is dominated by the absorption of a substance (e.g. water in case the material is skin) that is contained in the material in large quantities so that its percentage in the material is not varying substantially. In other words, the reference measurements do not serve to measure the absorption of the analyte, but the absorption of other specific substances in the material or of the material background. Then, these response signals obtained for the reference measurements are used for improving the analyte measurement procedure “on-the-fly”, which is possible since these reference measurements are carried out concurrently with the analyte measurement procedure.

According to one variant, the response signals obtained for the reference measurements are used for calibrating an excitation radiation source for generating said excitation radiation. For example, in typical analyte measurement procedures, a sequence of analyte-wavelength-specific measurements are carried out with different analyte-characteristic-wavelengths, leading to corresponding response signals. The inventors have noticed that even during the course of fairly short analyte measurement procedures, during which the thermal or pressure transmitting contact between the material and the measurement body is maintained and which may last on the order of tens of seconds only, there can be significant variations in the power of the excitation radiation source, or variations in the optical contact between the material and the measurement body, or both, which have an impact on the analysis result, since it will change the measured absorption of different analyte-characteristic-wavelengths of the same analyte. While the skilled person might consider carrying out a calibration measurement using a reference wavelength different from the analyte-characteristic-wavelengths prior to the actual analyte measurement procedure, the inventors surprisingly found out that in practice, there are significant variations in the power of the radiation source and the optical coupling between the material on the measurement body on much shorter timescales, which can better be properly accounted for using the reference measurements carried out concurrently and interleaved with the measurement of the analyte absorption. The reference measurements then allow for calibrating the excitation radiation source, to avoid power fluctuations thereof or to account for changes in the optical coupling between the material and the measurement body, to thereby significantly increase the accuracy of the analyte measurement procedure.

Similarly, the response signals obtained for the reference measurements may be used for calibrating the detection device “on-the-fly”, thereby allowing for accounting for fluctuations in the detection device itself, or to correct for other sources of fluctuations that can be compensated by calibration of the detection device.

In addition or alternatively, the response signals obtained for the reference measurements may be used to recognize a variation in the measurement conditions by comparing the results of individual reference measurements.

In addition or alternatively, the response signals obtained for the reference measurements may be used for adapting the analyte measurement procedure with respect to one or more of the entire duration thereof, the absolute or relative duration of analyte-wavelength-specific measurements for a given analyte-characteristic-wavelength, and/or terminating and restarting the analyte measurement procedure. For example, if the reference measurements indicate that there are large fluctuations in the measurement conditions, this could be an indication to prolong the analyte measurement procedure, such as to compensate for possibly more noisy data with longer measurement times. In addition or alternatively, it may be the case that the reference measurements indicate variations in the measurement conditions occurring only during certain time portions of the entire analyte measurement procedure, and in this case it would be sufficient to devote extra measurement time on those analyte-characteristic wavelengths that have been used during this time portion. The inventors found that this way, the overall quality and consistency of the measurement can be significantly improved without having to repeat the measurement or dramatically increase the measurement time.

In addition or alternatively, the response signals obtained for the reference measurements may be used for terminating and possibly restarting the analyte measurement procedure, if the reference measurements indicate that the reliability of the measurement is doubtful. With respect to the specific example of glucose measurement, this may for example apply for cases where the finger is not placed properly on the measurement body and where it would be advisable to lift and reposition the finger once more and simply start the measurement procedure again. It is much more user-friendly if this can be determined quickly, i.e. during the ordinary duration of an analyte measurement procedure, rather than asking the patient to repeat the measurement after the full analyte measurement procedure and the corresponding analysis has been finished. This also makes it possible to initiate various attempts without frustrating the user.

Instead of or in addition to carrying out the calibration of the excitation radiation source or the detection device, or instead of or in addition to adjusting the absolute or relative duration of the analyte-wavelength-specific measurements for certain analyte-characteristic-wavelengths, it is also possible to adapt the analysis carried out in the analyzing step to account for distortions and fluctuations assessed by the reference measurements in a mathematical way, taking into account the timing information associated with the respective reference measurements. This could for example comprise normalizing results of at least some of the analyte-wavelength-specific measurements based at least in part on the results of one or both of a respective preceding or succeeding reference measurement, e.g. based on an interpolation of various reference measurement results.

In preferred embodiments, between at least 25%, preferably between at least 50% of each pairs of successive analyte-wavelength-specific measurements, a reference measurement is carried out. In addition or alternatively, said reference measurements are carried out at an average rate of at least once every 5 seconds, preferably at least once per second, and most preferably at least 10 times per second. It has been found in practice that this close monitoring by reference measurements allows for significantly improving the accuracy of the analyte measurement procedure and the corresponding analysis.

This finding is quite surprising for the person skilled in the art, because the reference measurements per se do not directly contribute to information about the analyte, and any time spent for the reference measurement cannot be devoted to the analyte-wavelength-specific measurements. In many applications, and in particular when it comes to non-invasive glucose measurement, the measurement times are limited for practical reasons, and the obvious consequence of the limited time would be to devote as much of the precious measuring time to those wavelengths that allow for detecting absorption of the analyte. However, the inventors have found that in practice, even for a given, limited overall measurement time, the results become more accurate when devoting some of the measurement time for the interspersed reference measurements.

In an alternative embodiment, during said analyte measurement procedure, a sequence of analyte-wavelength-specific measurements is carried out while maintaining said thermal or pressure transmitting contact between the material and the measurement body, wherein in each analyte-wavelength-specific measurement, excitation radiation with an analyte-characteristic-wavelength selected from a predetermined set of analyte-characteristic-wavelengths is irradiated and a corresponding response signal is obtained, and wherein a quality assessment is carried out based on the response signals associated with one or more analyte-characteristic-wavelengths, and wherein based on said quality assessment, the measurement time devoted to the corresponding one or more analyte-characteristic-wavelengths during the current analyte measurement procedure or one or more future analyte measurement procedures is adjusted, or the relative weight associated with the corresponding analyte-wavelength-specific measurement in the analysis is adjusted.

In a preferred embodiment, said quality assessment is carried out during said analyte measurement procedure and the measurement time devoted to the corresponding one or more analyte-characteristic-wavelengths is adjusted in real time during said analyte measurement procedure.

In addition or alternatively, said quality assessment is based, at least in part, on one or more of

- a signal-to-noise ratio of said response signal or a quantity derived therefrom, and
- the result of one or more reference measurements, in which excitation radiation with a reference wavelength is irradiated into the material and a corresponding response signal is obtained, wherein said reference wavelength is a wavelength at which the absorption of said analyte is low. For example, the reference wavelength may be the wavelength for which the absorptivity of the analyte is less than 30%, preferably less than 20%, more preferably less than 10% and most preferably less than 5% of the absorptivity at the highest absorption peak associated with any of the analyte-characteristic-wavelengths relied on in the analyte measurement procedure.

In a preferred embodiment the method further comprises a material status analyzing procedure, in which the present status of the material is analyzed based on one or more of

- one or more response signals established when the material is irradiated with excitation radiation at a wavelength different from said analyte-characteristic-wavelengths,
- one or more response signals established for excitation radiation with the same analyte-characteristic-wavelengths as used in the analyte measurement step, but for at least partially different intensity modulation frequencies of said excitation radiation than in the analyte measurement step, and
- one or more measurements related to the material status carried out with additional sensor equipment.

Then, based on a result of said material status analyzing procedure, at least one of

- a selection of analyte-characteristic-wavelengths used during said analyte measurement procedure, or relied on during said analysis,
- an absolute time or a relative time proportion of use of analyte-characteristic-wavelengths during said analyte measurement procedure, or a relative weight given to the wavelengths in the analysis,
- a selection of analyte-characteristic-wavelengths to be used simultaneously during said analyte measurement procedure, and
- a selection of one or more main frequencies of the modulation of said excitation radiation intensity to be used during said analyte measurement procedure is determined.

According to this aspect of the invention, the method comprises a specific material status analyzing procedure, in which the status of the material is analyzed. Simply speaking, this "material status" analysis is directed to the state of the material with respect to criteria other than the analyte itself or other substances than the analyte which are contained in the material, but that can be accounted for in the analyte measurement procedure to allow for optimum measurement accuracy and/or efficiency of the analyte measuring procedure.

In particular, the material status analyzing procedure may involve a collection of response signals established when the material is irradiated with excitation radiation at a wavelength that is different from said analyte-characteristic-wavelengths, typically at a wavelength where the absorptivity of the analyte is low, and even lower than in all or at least most of the above-mentioned local minima in the absorption spectrum, where the absorption will often still be appreciable. In particular, at these wavelengths the analyte may have an absorptivity that is less than 30%, preferably less than 20%, more preferably less than 10% and most preferably less than 5% of the absorptivity at the highest absorption peak associated with any of the analyte-characteristic-wavelengths relied on in the analyte measurement procedure. Accordingly, using the response signals established when the material is irradiated with excitation radiation at wavelength different from the analyte-characteristic-wavelengths, the presence and concentration of substances other the analyte can be determined, which may correspond to one aspect of the material status.

In addition or alternatively, the material status analysis procedure may involve one or more response signals established for excitation radiation with the same analyte-characteristic-wavelengths as used in the analyte measurement step, but for at least partially different intensity modulation frequencies of said excitation radiation than in the analyte measurement step. As will become apparent from the detailed description below, this way for example the suitable or optimized depth range within the material for measuring the analyte can be determined. Herein, the expression "at least partially different intensity modulation frequencies" indicates that some of the intensity modulation frequencies employed in the material status analysis procedure for a given analyte-characteristic-wavelength may likewise be used in the analyte measurement procedure, but not all of them. Typically, a larger number of modulation frequencies may be tested in the material status analysis procedure, and only a subset thereof will be used in the analyte measurement procedure.

In addition or alternatively, the material status analyzing procedure may involve one or more measurements related to the material status carried out with additional sensor equipment, i.e. with sensor equipment that is per se unrelated to the analyte measurement procedure.

The additional information about the material status obtained in the material status analyzing procedure can then be used to improve the efficiency and/or accuracy of the analyte measurement procedure. In particular, based on a result of the material status analyzing procedure, an optimum selection among various possible analyte-characteristic-wavelengths that are actually used during the analyte measurement procedure can be made. This way, the analyte measurement procedure can be limited to those analyte-characteristic-wavelengths for the excitation radiation which—in consideration of the material status established by the material status analyzing procedure—are expected to give the best, e.g. most specific, analyte measurement results, thereby improving the efficiency, reliability and accuracy of the analyte measurement procedure. Instead of selecting the analyte-characteristic-wavelengths to be used during the analyte measurement procedure, it is also possible to only select those analyte-characteristic-wavelengths on which the analysis in the analyzing step shall rely. That is to say, instead of omitting a possible analyte-characteristic-wavelength during the analyte measurement procedure, it is likewise possible to simply disregard the measurement based on this analyte-absorption wavelength during the analyzing step, or to account for it with a reduced weight. Nevertheless, for the purpose of reducing the measurement times, it is preferred to actually make a selection regarding the possible analyte-characteristic-wavelengths to be used during the analyte measurement procedure.

Instead of selecting analyte-characteristic-wavelengths as a whole, it is also possible to select, based on the result of the material status analyzing procedure, an absolute time or a relative time proportion of use of analyte-characteristic-wavelengths during the analyte measurement procedure, or a relative weight given to the wavelengths in the analysis. According to this variant, more measurement time may be devoted to those analyte-characteristic-wavelengths which—in view of the results yielded by the material status analyzing procedure—are expected to contribute more to an accurate analysis result. This way again, the efficiency of the analyte measurement procedure can be increased.

In a further variant, the result of the material status analyzing procedure may suggest a selection of analyte-characteristic-wavelengths to be used simultaneously during the analyte measurement procedure. This way, by using two or more different analyte-characteristic-wavelengths simultaneously as excitation radiation, the efficiency of the analyte measurement procedure can be further increased.

Finally, in addition or alternatively, the result of the material status analyzing procedure may suggest a favorable selection of one or more main frequencies of the modulation of the excitation radiation intensity to be used during the analyte measurement procedure. Herein, the expression "main frequency" of the modulation refers to the frequency of the dominant frequency in the Fourier spectrum of the modulation function. For example, if the modulation function is a periodic square wave function, the main frequency would be the inverse of the period thereof. As the modulation frequency of the excitation radiation is also one of the major factors determining the depth in which, predominantly, the measurement of the analyte is carried out, the optimized depth of the measurement may be determined by the step of material status analysis by using signals that may be provided by other substances than the analyte which are present in the material and of which in some cases the profile of density versus the depth under the surface of the material is known beforehand.

In summary, by combining the analyte measurement procedure with the material status analyzing procedure described herein, and by further determining optimum choices for analyte-absorption wavelengths and/or modulation frequencies to be used during the analyte measurement procedure based on the determined material status, the accuracy and efficiency of the analyte measurement procedure and the analysis based thereon can be improved.

In preferred embodiments, the material is human tissue, in particular human skin, and said analyte is glucose present in the skin, in particular the interstitial fluid thereof. While in the following explanations and in the description of the specific embodiments reference is made to this embodiment, is to be understood that the invention is not limited to this, and that it can be applied to other types of materials and analytes.

In preferred embodiments, the material status analyzing procedure is carried out interleavedly or timewise overlapping with the analyte measurement procedure. In other words, in these preferred embodiments, an analyte measurement procedure that relates to the same analyzing step is carried out intermittently or in turn with material status analyzing procedures carried out in between. Namely, the inventors noticed that best results can be achieved if the material status is established with minimum time delay with respect to the analyte measurement procedure and hence reflects the current status of the material applying during the analyte measurement procedure as closely as possible. In other embodiments, the material status analyzing procedure may be carried out first, and the analyte measurement procedure may be carried out thereafter. However, in this case, the material status analyzing procedure is preferably carried out in less than five minutes, preferably less than three minutes, and most preferably less than one minute prior to the beginning of the analyte measurement procedure.

In preferred embodiments, the thermal or pressure transmitting contact between the material and the measurement body is maintained during a time interval including at least part of said material status analyzing procedure and the analyte measurement procedure. For example, if the analyte is glucose and the "material" is skin of the fingertip placed on the measurement body, this means that that the finger tip is maintained on the measurement body steadily throughout both, the material status analyzing and the analyte measurement procedures.

In preferred embodiments, the material status comprises the presence and/or concentration of perturbing substances within said material that are different from said one or more analytes but exhibit significant absorptivity of excitation radiation at at least one of said analyte-characteristic-wavelengths. An example for such perturbing substance in the case of the glucose measurement in in the interstitial fluid of human skin would be the presence of lactate, the level of which differs not only from person to person, but changes for each individual based for example on recent physical exercise and the like. The lactate absorption spectrum overlaps with absorption peaks of glucose and can therefore perturb the measurement results. Then, in case said material status analyzing procedure yields a sufficiently high concentration of said perturbing substances, the use of the at least one of said analyte-characteristic-wavelengths where said perturbing substances exhibit significant absorptivity is avoided or suppressed, or the respective wavelength is shifted away from the absorption maximum of the perturbing substance. Other examples of a perturbing substance could be fatty acids, cosmetics, gels, such as gels used for ultrasound diagnostics, excess water, or albumin.

In a preferred embodiment related to the measurement of glucose in human tissue, the said at least one main frequency of the modulation of said excitation radiation intensity to be used during said analyte measurement procedure comprise a first main modulation frequency and a second main modulation frequency, wherein said first main modulation frequency is chosen sufficiently low such that the response signal reflects at least in part absorption of excitation radiation within the interstitial fluid, wherein the second main modulation frequency is higher than the first main modulation frequency, and wherein in said analysis, response signals corresponding to said first and second main modulation frequencies, or quantities derived therefrom, are mathematically combined, e.g. by subtraction from one another or division of one through the other, to yield information indicative of the absorption in the interstitial fluid. Herein, the second main modulation frequency may be higher than the first main modulation frequency by a factor of at least 1.5, preferably at least 2.0, and most preferably at least 3.0. In some embodiments, the first main modulation frequency may be in a range of 20 to 30 Hz, while the second main modulation frequency could be in a range from 150 to 300 Hz.

When the excitation radiation is radiated into the material, part of it will be absorbed along its light path, i.e. at different depths below the surface of the material. In response to the absorption, a heat signal is generated, which diffuses back to the surface of the material and is received by the measurement body. Since the intensity of the excitation radiation is modulated, the material is heated by absorption in a time-dependent manner, leading to a temperature field that varies as a function of space and time and that is often referred to as a thermal wave. The term thermal "wave" is somewhat misleading, since the travel of heat through the material is not governed by a wave equation, but by a diffusion equation instead. This also means that the largest depth of the modulated absorption underneath the surface of the material that can be detected by heat received by the measurement body at the surface of the material is limited approximately by the so-called diffusion length $\mu_t$, which depends on the density $\rho$, the specific heat capacity $C_p$, and the thermal conductivity $k_t$ of the material as well as on the modulation frequency f of the excitation radiation:

$$\mu t(f) = \sqrt{\frac{kt}{\rho \cdot Cp \cdot 2f}}$$

Since the interstitial fluid is only found in the tissue at a certain range below the surface of the skin, in order to generate response signals indicative of absorption in the interstitial fluid, the modulation frequency of the excitation radiation has to be indeed "sufficiently low" such that the diffusion length $\mu_t$ is long enough to cover the distance between regions with interstitial fluid and the skin surface. However, as explained above, the diffusion length depends on the physical properties of the tissue, namely density $\rho$, the specific heat capacity $C_p$, and the thermal conductivity $k_t$, and the inventors noticed that these properties will not only vary from person to person, but may also vary for the same person with time, depending for example on whether the skin is dry or moist, whether the skilled person has used hand moisture lotion, or the like. In other words, the thermal diffusion length as a function of frequency is a material status that for best results should be assessed at or close to the time of the analyte measurement procedure in the material status analyzing procedure.

Moreover, the depth below the surface at which the interstitial fluid resides is found to be dependent on the thickness of the stratum corneum, which again does not only vary from person to person, but also varies for the same person over time and also over the location of the skin surface where the measurement takes place. For example, if a person has recently done physical work with his or her hands, or has practiced a string instrument, the stratum corneum may be thicker than usual, meaning that the absorption has to be effected in deeper layers below the surface of the skin in order to cover the interstitial fluid. Again, the thickness of the stratum corneum is a "material status" that can be assessed in said material status analyzing procedure.

Accordingly, determining a first main modulation frequency that is "sufficiently low" such that the response signal reflects at least in part absorption of excitation radiation within the interstitial fluid can best be done in the material status analyzing procedure.

However, even if the thermal diffusion length is sufficiently long that the response signal reflects at least in part absorption of excitation radiation with interstitial fluid, the response signal will also represent any absorption in upper layers of the skin, in particular the stratum corneum, and hence include a contribution that is not related to the glucose within the interstitial fluid. Indeed, this contribution from upper layers of the skin, in particular the stratum corneum, will be typically overrepresented in the response signal, since the intensity of the excitation radiation in the upper layers is higher than deeper into the skin, and since the absorption heat needs to travel only a shorter distance from the upper layers to reach the measurement body. In order to estimate this contribution of higher layers of the skin to the first response signal, at least one additional second response signal is recorded in response to excitation radiation with said second main modulation frequency, which is higher than the first main modulation frequency, and hence leads to a shorter diffusion length and therefore represents absorption predominantly in the upper layers of the skin above the region where the interstitial fluid resides. Then, response signals corresponding to said first and second main modulation frequencies, or quantities derived therefrom, are mathematically combined to yield information more specifically indicative of the absorption in the interstitial fluid. There are different ways of mathematical combining these response signals, and this aspect of the invention is not limited to any single one of them. For example, the second response signal can be multiplied with a normalizing factor that is obtained e.g. based on reference measurements with excitation wavelength(s) for which glucose absorption is negligible, and then the product may be subtracted from the first response signal.

At first sight, one could believe that it would be easy to choose a first main modulation frequency that is "sufficiently low" such that the response signal reflects at least in part absorption of excitation radiation within the interstitial fluid, namely by choosing arbitrarily low modulation frequencies leading to very long diffusion lengths, to thereby ensure that the interstitial fluid is covered thereby. However, the inventors have noticed that while it is important that the diffusion length covers the depth region where the interstitial fluid resides, the response signal quality and measurement accuracy can be significantly improved if excessively long diffusion lengths are avoided. Indeed, the inventors have noticed that particularly good results can be obtained if the thermal diffusion length is at most approximately equal to the optical absorption length for the excitation radiation and at least half as long as the optical absorption length, and if the first modulation frequency is chosen accordingly.

Without wishing to be bound by theory, this finding can be understood as follows: the optical absorption length $\mu_\alpha(\lambda)$ for radiation with a wavelength $\lambda$ within the material, in particular human tissue, is the inverse of the absorption coefficient $\alpha(\lambda)$, i.e. $\mu_\alpha(\lambda)=1/\alpha(\lambda)$. The optical absorption length $\mu_\alpha(\lambda)$ corresponds to an optical path length within the material in which the intensity of radiation with a wavelength $\lambda$ has dropped by a factor 1/e due to absorption. In order to detect the concentration of the analyte, such as glucose, one wishes to effectively measure a signal that is proportional to the absorption coefficient $\alpha(\lambda)$ at an analyte-characteristic-wavelength $\lambda$, since the concentration of the analyte is proportional to the absorption coefficient $\alpha(\lambda)$. For this purpose, however, the penetration depth of the excitation radiation should be longer than the thermal diffusion length. This becomes plausible by considering the opposite scenario, in which the optical absorption length is smaller than the thermal diffusion length: in this case, almost the entire optical energy would be absorbed within the depth range corresponding to the thermal diffusion length, and would be represented by the response signal. In other words, the response signal would essentially represent the energy of the excitation beam rather than the specific absorption by the analyte. Accordingly, it is necessary that only a part of the entire excitation radiation is absorbed within the thickness range contributing to the thermal signal recorded at the surface of the material by means of said response signal; in this case, the response signal indeed rises and falls according to the absorption coefficient.

Accordingly, one would expect that useful response signals would require that $\mu_t(f)<\mu_\alpha(\lambda)$. A reasonable lower boundary $f_{min}$ for the modulation frequency f can therefore be defined as the frequency at which $\mu_t(f_{min})=\mu_\alpha(\lambda)$, which leads to $f_{min}=k_t\cdot\alpha(\lambda)^2/(2\cdot\rho\cdot C_p)$. The inventors have found that indeed optimum modulation frequencies f to be used as the lower, first modulation frequency are within a range $4\cdot f_{min}>f>f_{min}$, preferably $3\cdot f_{min}>f>f_{min}$, and more preferably $2\cdot f_{min}>f>f_{min}$.

While it has been shown above how the optimum first modulation frequency depends on physical parameters of the tissue, such as $k_t$, $\rho$, $C_p$, $\alpha(\lambda)$, this does not mean that in practice the modulation frequency is to be determined by determining each of these parameters individually and then calculating it as defined above. However, what this does show is how the optimum first modulation frequency depends on tissue parameters, and hence the "material status" of the tissue or skin, which may change from person to person, and may vary even for the same individual with time. This demonstrates why indeed the accuracy efficiency of the analyte measurement procedure can be improved by carrying out the "material status analyzing procedure", and by selecting one or more main frequencies of the modulation of the excitation radiation intensity to be used during the analyte measurement procedure based on the material status analyzing result.

In a preferred embodiment, the material status comprises the water content of the skin. Preferably, the water content of the skin is measured using a dedicated corneometric device. This corneometric device is an example of the "additional sensor equipment" referred to above. For reasons explained below in more detail, the analyte measurement procedure can be optimized in various ways to account for the water content of the skin.

As the skilled person will appreciate, the water content of the skin is a material status that tends to vary significantly not only from person to person, but also for the same individual, since it may depend e.g. on the climate conditions, whether the individual has recently washed his or her hands, recently used moisturizing lotion or the like. Accordingly, it is advantageous to assess the water content of the skin during or directly before carrying out the analyte measurement procedure in said material analyzing procedure. Then, knowledge about the water content will allow for choosing suitable analyte-characteristic-wavelengths and/or suitable modulation frequencies for the modulation of the excitation radiation.

In a preferred embodiment, in case a higher water content is determined in said material analyzing procedure, shorter wavelengths among a set of predetermined analyte-characteristic-wavelengths are preferentially used in the analyte measurement procedure. "Preferentially using" shorter wavelengths could mean that shorter wavelengths among said set of predetermined analyte-characteristic-wavelengths are selected for use while one or more longer wavelengths among said set of predetermined analyte-characteristic-wavelengths are not used. In addition or alternatively, this could mean that all wavelengths of said predetermined set of analyte-characteristic-wavelengths are used, but that the relative time devoted to the shorter wavelengths is longer than that that devoted to one or more of the longer wavelengths. In practice, such selection of wavelengths can be made in various ways, and this embodiment is not limited to any specific one of them.

For example, in a simple embodiment, there could be a predefined threshold value for the water content (or another parameter related to it), and if the water content is above the threshold, it is considered "high", and it is considered "low" if the water content is below this threshold. Two different subsets among said set of predetermined analyte-characteristic-wavelengths may be predefined to be used in case of "high" and "low" water content, respectively, wherein the average excitation radiation wavelength in the subset associated with "high" water content is shorter than in the subset associated with the "low" water content. However, in other embodiments there may be different subsets of analyte-characteristic-wavelengths to be used for different measured ranges of water content. In a yet further embodiment, a selection function may be employed that defines the selection of excitation wavelengths as a function of a determined water content value according to some mathematical rule. Any of these embodiments may be used, as long as it is ensured that in case of higher water content, with all other characteristics of the material status the same, shorter excitation wavelengths are preferentially or predominantly used.

The rationale behind this selection of excitation wavelengths is that water has a fairly high and wavelength-unspecific absorption coefficient and hence tends to attenuate the excitation radiation in the relevant spectral range. Accordingly, even if the excitation wavelength is chosen to coincide with an absorption peak of the analyte (e.g. glucose), water will contribute to the absorption coefficient $\alpha(\lambda)$, and hence effectively reduce the optical absorption length $\mu_\alpha(\lambda)$. This reduces the accessible depth of the measurement within the material (tissue), bearing in mind from the above explanations that the optical absorption length $\mu_\alpha(\lambda)$ should not be less than the thermal diffusion length $\mu_t(f)$. However, in the wavelength region including the most useful absorption peaks of glucose for the purposes of the invention, i.e. a region between roughly 8 μm to 10 μm, the absorption coefficient $\alpha(\lambda)$ of water is found to decrease with decreasing wavelength, such that the problems associated the absorption by water are less severe for short excitation wavelengths. Accordingly, if as part of the material status analyzing procedure a higher water content is determined, this leads to a selection of shorter excitation wavelengths in the analyte measurement procedure.

In addition or alternatively, at least one of the one or more main frequencies of the modulation of said excitation radiation intensity used during said analyte measurement procedure is/are adapted to the water content determined in said material analyzing procedure in such a way that with all other characteristics of the material status the same, higher main frequencies of the modulation are chosen for higher water contents. In other words, when the water content is found to be high, at least one of the one or more main frequencies of the modulation of the excitation radiation intensity is increased, such as to effectively lower the thermal diffusion length $\mu_t$ (f) such as to better match or stay below the optical absorption length $\mu_\alpha(\lambda)$, which is likewise expected to decrease due to the increased absorption of water. Again, there are many ways to choose the one or more main modulation frequencies in response to the determined water content, and this aspect of the invention is not limited to a single one of them. For example, in one embodiment, a water content threshold can be defined, and depending on whether the water content is above or below this threshold, a higher or lower modulation frequency can be chosen. Alternatively, various water content ranges could be predefined, and for each water content range, a corresponding main modulation frequency could be predefined, where higher modulation frequencies are associated with higher water contents. In a yet further embodiment, the modulation frequency or frequencies could be determined as a function of the water content, and possibly additionally as a function of the excitation radiation wavelength, such that higher modulation frequencies are chosen for higher water contents and optionally also for longer excitation radiation wavelengths, to account for the fact that the absorption coefficient $\alpha(\lambda)$ of water decreases with wavelength. Irrespectively of precisely how the modulation frequency or frequencies are adapted to the water content, in any case the selection is such that with all other characteristics of the material status the same, higher main frequencies of the modulation are chosen for higher water contents.

In a preferred embodiment, the material status comprises the thickness of the stratum corneum overlying the interstitial fluid. As mentioned above, the thickness of the stratum corneum differs not only from person to person, but may significantly change over time for the same individual, depending on the amount of recent physical work or exercise. Accordingly, the accuracy and efficiency of the analyte measurement procedure can be significantly increased if it is adapted to the actual thickness of the stratum corneum, which is to be individually assessed during or before the analyte measurement procedure is carried out.

In a preferred embodiment, the thickness of the stratum corneum is directly or indirectly assessed based on response signals established for identical wavelengths of the excitation radiation but for different intensity modulation frequencies of said excitation radiation, wherein said wavelength is chosen to match an absorption band of a substance present with different concentrations in the stratum corneum and the interstitial fluid, respectively. As explained before, the modulation frequency of the excitation radiation governs the thermal diffusion length and hence the depth range in which absorption processes can be detected by received thermal signals. Thus, by varying the intensity modulation frequencies, absorption in different depth ranges can be measured. And since the wavelength of excitation radiation matches an absorption band of a substance that is present with different concentrations in the stratum corneum and in the interstitial fluid, the thickness of the stratum corneum can be estimated by means of depth-depended absorption.

Note that the thickness of the stratum corneum may be directly assessed, in the sense that a certain thickness in mm is determined, or indirectly, for example by simply determining modulation frequencies corresponding to the boundary region between the stratum corneum and the interstitial fluid, which would be an indirect or implicit measure of the stratum corneum thickness. In some embodiments, the absorbing substance present with different concentration in the stratum corneum and interstitial fluid may be the analyte itself, such as the glucose. Among the different intensity modulation frequencies, there will be higher frequencies, corresponding to shorter thermal diffusion lengths where no absorption attributable to glucose is measured, which indicates that this depth corresponds to the stratum corneum. Conversely, among the different intensity modulation frequencies, there will be lower modulation frequencies, corresponding to longer thermal diffusion lengths, where significant glucose absorption is detected, indicating that this depth corresponds to the depth in which the interstitial fluid resides. Herein, the absorption "attributable" to glucose can be determined relying on reference measurements with wavelengths where the local absorption is negligibly low, but the other absorption background, in particular due to water, is expected to be very similar.

In a preferred embodiment, at least one of the one or more main frequencies of the modulation of said excitation radiation intensity used during said analyte measurement procedure is/are adapted to the thickness of the stratum corneum overlying the interstitial fluid determined in said material analyzing procedure in such a way that with all other characteristics of the material status the same, a lower main frequency of the modulation is chosen for higher stratum corneum thicknesses. Again, there are various ways of adjusting the main frequencies of the excitation radiation intensity modulation as a function of the stratum corneum thickness. For example, similar to the previous embodiments, there could be a predetermined threshold value of the stratum corneum thickness (or another parameter representing the same), and the modulation frequency could be adjusted based on whether the stratum corneum thickness is below the threshold (in which case the higher modulation frequency would be chosen) or above the threshold (in which case the lower modulation frequency would be chosen). In alternative embodiments, there could again be several stratum corneum thickness ranges and associated modulation frequencies, where the modulation frequencies for larger stratum corneum thicknesses are lower than for smaller stratum corneum thicknesses. In yet further embodiments, the modulation frequency could be determined based on a continuous function relating modulation frequencies to be used in the analyte measurement procedure with stratum corneum thicknesses determined in the material status analyzing procedure. Any way of selecting the modulation frequency as a function of determined stratum corneum thickness may be employed, as long as it is ensured that with all other characteristics of the material status the same, a lower main frequency of the modulation is chosen for higher stratum corneum thicknesses. It is further noted that instead of determining the thickness of the stratum corneum by measurements with different excitation radiation intensity modulation frequencies, it is likewise possible to measure its thickness using a dedicated sensor or measuring device, for example an ultrasound sensor or an OCT device.

Note that when referring to choosing the "one or more" main frequencies of the modulation in consideration of the stratum corneum thickness, this could apply both, to the first (lower) modulation frequency intended to cover significant portions including interstitial fluid, as well as and the second (higher) modulation frequency, which is intended to measure response signals for compensating the absorption in higher layers of the skin where no or little interstitial fluid is present, in particular the stratum corneum. In preferred embodiments, at least the second modulation frequency is adapted to the determined thickness of the stratum corneum. However, it is also possible that only the first modulation frequency is adapted to the determined thickness of the stratum corneum.

In preferred embodiments, the material status comprises the pH value of the skin. Herein, the pH value is preferably determined using said additional sensor equipment formed in this case by a dedicated pH measuring device. In case the pH value determined in said material analyzing procedure is found to be a lower value, with all other characteristics of the material status the same, analyte-characteristic-wavelengths overlapping with absorption bands of lactate are used less preferentially in the analyte measurement procedure than in case the pH is found to be a higher value.

The rationale behind this embodiment is that it has been found that lower pH values of the skin are often an indication of higher lactate concentrations in the skin. Accordingly, in case of a low pH value and hence reasonable expectation of higher lactate concentration, it would be preferable to avoid analyte-characteristic-wavelengths in the analyte measurement procedure that overlap with the lactate absorption bands, or to at least devote less measuring time to them. For example, one or more threshold values for the pH could be defined, and depending on whether the pH is above or below such threshold, the degree of use of an overlapping analyte-characteristic-wavelength could be adapted, including the case that this overlapping analyte-characteristic-wavelength is not used at all in the analyte measurement procedure.

In a preferred embodiment, the skin forming the material is skin at the fingertip of a human subject, and the material status comprises the average height of the epidermal ridges. The average height of the epidermal ridges is preferably estimated using said additional sensor equipment formed by a dedicated fingerprint sensor.

Herein, the power of the excitation radiation used in the analyte measurement procedure is preferably adapted as a function of the average height of the epidermal ridges in such a manner that, with all other characteristics of the material status the same, the power of the excitation radiation used in the analyte measurement procedure is increased for higher average epidermal ridges. The inventors have noticed that in case of high epidermal ridges, the optical contact between the measurement body and the finger tip resting thereon may be inferior such that a lower fraction of the excitation radiation will actually be coupled into the finger tip. This may be compensated by detecting higher epidermal ridges during the material status analyzing procedure and increasing the power of the excitation radiation to account for the expected loss at the interface. Note that the "average height of the epidermal ridges" corresponds to the average height in this situation when the fingertip is actually pressed against the measurement body and therefore depends on both, the structure of the epidermis but also on the current contact pressure, which may vary between different measurement sessions for the same person. This is why it is advantageous to account for it in the material status analyzing procedure that is associated with a given analyte measuring procedure. Moreover, the "average height of the epidermal ridges" need not be determined in an overly precise manner, in many cases a qualitative assessment ("low", "normal" and "high") or estimation already serves the purpose. In some embodiments, the height of the epidermal ridges is estimated based on the distance between adjacent epidermal ridges, as these two quantities are typically correlated. The fingerprint can be assessed for example using a capacitive measurement using technology per se known from fingerprint sensors in the art.

The actual mapping between the additional power of the excitation radiation and the detected average height of the epidermal ridges can be carried out in many ways, and this embodiment is not limited to any specific one of them. In simple variants, as mentioned before, there would be rough classifications of the detected average epidermal ridges, such as "low", "normal" and "high", and each of these classes will be associated with a corresponding power or power correction of the excitation radiation. In other embodiments, only two or more than three of these classes could be defined, and in yet further embodiments, the power could be a continuous function of the average epidermal ridge height or a parameter related to it (such as the average distance between two adjacent epidermal ridges). Any of these variants would be possible embodiments, as long as it is ensured that—with all other characteristics of the material status the same—the power of the excitation radiation used in the analyte measurement procedure is generally increased for higher average epidermal ridges.

In yet further embodiments, the material status comprises the temperature of the skin.

In a preferred embodiment, the time modulation of said intensity of said excitation radiation is chosen such that the envelope of the intensity is asymmetrical in that the proportion of time during which the envelope assumes 50% or more of the average intensity is less than 50%, preferably less than 46% and most preferably less than 43% of the total time. However, the proportion of time during which the envelope is less than 50% should not be chosen too low, and is preferably at least 20%, more preferably at least 30%.

The obvious choice for the modulation function of the excitation radiation intensity is a square wave function alternating between zero ("off") and a maximum value ("on") where the length of the on-intervals and the off-intervals are identical. However, the inventors have found that surprisingly the accuracy and efficiency of the analyte measurement procedure can be improved if e.g. the relative length of off-intervals is longer than that of the on-intervals, without changing the main frequency or period of the modulation signal, which period is the sum of the on- and off-intervals.

So far, the main focus of the considerations regarding the intensity modulation of the excitation radiation was on the corresponding thermal diffusion length, but according to the theoretical understanding and practical experience of the inventors, the thermal diffusion length is not or at least not noticeably affected by merely increasing the relative proportion of the off-times over the on-times. This notwithstanding, the inventors found that for the same overall frequency, better signal-to-noise ratios of the response signals can be obtained if the off-intervals are made longer and the on-intervals shorter. According to the understanding of the inventors, this is due to the fact that the response signals are essentially “AC signals”, in the sense that only the variation of the response signal with time can be assessed for estimating the degree of absorption. For this, it appears to be important that the physical response of the measurement body due to the heat received from the material (such as the formation of the thermal lens leading to a deflection of a detection beam) can more fully decay before the next heat pulse is received. This would explain why by increasing the off-intervals, the AC-signal can be improved, since there is relatively more time for the physical response of the measurement body to decay.

The modulation functions considered herein are not limited to square wave functions, and it is noted that for arbitrary modulation functions, similar effects can be obtained if the low intervals of the modulation functions are longer than the high intervals. For this reason, according to this embodiment, the time modulation of said intensity of said excitation radiation is chosen such that the envelope of the intensity is asymmetrical in that the proportion of time during which the envelope assumes 50% or more of the average intensity is less than 50%, preferably less than 46% and most preferably less than 43% of the total time, and preferably at least 20%, more preferably at least 30%.

In addition or alternatively, the time modulation of said intensity of said excitation radiation is chosen such that the envelope of the intensity follows a periodically repeating pattern, wherein said pattern includes a high intensity time portion including more than 80% of the intensity-time-integral and a low intensity time portion including less than 20% of the intensity-time-integral of the pattern, wherein the ratio of the durations of the high and low intensity time portions is less than 0.9, preferably less than 0.8, and most preferably less than 0.7. However, in preferred embodiments, this ratio should be at least 0.4, and preferably at least 0.5.

The use of square wave modulation functions for the excitation radiation intensity has two general advantages. The first advantage is that for generating heat pulses, sharp excitation pulses with steep flanks promise to give particularly good results. The second advantage is that the square wave modulation is the easiest to establish in practice.

Nevertheless, the present inventors found that in spite of the apparent advantages of square wave modulations of the excitation light intensity, a sinusoidal modulation function may give better results in some applications, including the non-invasive glucose measuring in the skin of the user as described herein. This is a surprising finding, because the sinusoidal modulation function does not have the same sharp impulses found for square wave modulations which lead to particularly pronounced heat pulses in the skin that can be detected well using the apparatus of the invention. However, the inventors found that this disadvantage can be overcompensated in specific situations applying for some of the embodiments described herein, where the analyte to be measured, e.g. glucose, is mainly located in deeper layers of the material (e.g. the skin), which is only assessed by smaller modulation frequencies. When using a square wave signal, one has to distinguish between the main frequency thereof, which is the inverse of the repetition period of the signal, and the higher harmonic contributions to the signal, that are found in a Fourier series decomposition of the square wave signal. These higher frequency contributions lead to response signals that correspond to absorption in shallower regions of the skin which are not of interest e.g. for the glucose measurement described herein.

Accordingly, in preferred embodiments, the time modulation of said intensity of said excitation radiation is chosen such that the envelope of the intensity is approximately harmonic such that in a Fourier decomposition of the intensity of the excitation radiation, of the total intensity associated with the dominant frequency and the $1^{st}$ to $9^{th}$ harmonics, at least 95% is associated with the dominant frequency and at least 97%, preferably at least 98% is associated with the dominant frequency and first harmonic. Herein, n-th harmonic is understood in the usual manner to have a frequency of $(n+1)\cdot f$, wherein f is the dominant frequency. In a sinusoidal function, i.e. a fully harmonic function, the entire intensity would be associated with the dominant frequency f. In preferred embodiments, the time modulation function of the intensity need not be precisely harmonic, but shall be “approximately” harmonic in the sense defined above, in that at least 95% of the intensity is in the ground mode associated with the dominant frequency, and in that at least 97%, preferably at least 98% is in the ground mode and in the first harmonic together.

In a preferred embodiment, said detection device comprises a light source for generating a detection light beam travelling through at least a portion of said measurement body or a component included in said measurement body, said physical response of the measurement body to heat received from said material upon absorption of said excitation radiation is a local change in the refractive index of said measurement body or said component, and said detection device is configured for detecting one of a change in the light path or a change in the phase of detection beam due to said change in refractive index and for generating a response signal indicative of said change in light path or phase of the detection beam.

In a preferred embodiment, said measurement body is transparent for said detection light beam, said detection light beam is directed to be totally or partially reflected at a surface of said measurement body that is in thermal pressure transmitting contact with said material, and wherein said detection device comprises a photodetector, in particular a position sensitive photodetector, capable of detecting a degree, in particular angle of deflection of said detection light beam due to said local change in refractive index.

In a preferred embodiment, said detection device comprises an interferometric device allowing for assessing said change in phase of the detection beam and generating a response signal indicative of said change in phase.

In a preferred embodiment, said measurement body or a component in said measurement body has electrical properties that change in response to a local change in temperature or a change in pressure associated therewith, and wherein said detection device comprises electrodes for capturing electrical signals representing said electrical properties.

In a preferred embodiment, said excitation radiation is generated using an array of lasers, in particular semiconductor lasers, further in particular quantum cascade lasers, each having a dedicated wavelength. Each of the lasers may have its own modulation device, or they may have a common modulation device and they may be controlled by a common or by individual controllers. The lasers of an array may be optically aligned in a way that allows for using a common optical path for the excitation beam and they may for example radiate into the material through a common light waveguide. The laser array may be combined on a single semiconductor chip.

In a preferred embodiment, said excitation radiation is generated using at least one tunable laser, in particular at least one tunable quantum cascade laser.

In a preferred embodiment, some or all of said excitation wavelengths are in a range of 5 μm to 13 μm, preferably 8 μm to 11 μm. In alternative embodiments, some or all of said excitation wavelengths are in a range of 3 μm to 5 μm. This wavelength range is for example useful for detecting absorption of $CH_2$ and $CH_3$ vibrations in fatty acids.

A further aspect of the invention relates to an apparatus of analyzing a material comprising at least one analyte, said apparatus comprising a measurement body having a contact surface suitable to be brought in thermal contact pressure transmitting contact with said material, said thermal or pressure transmitting contact permitting heat or pressure waves generated by absorption of excitation radiation in the material to be transferred to said measurement body, an excitation radiation source configured for irradiating excitation radiation into the material to be absorbed therein, a detection device for detecting a physical response of the measurement body, or of a component included therein, to heat or pressure waves received from said material upon absorption of said excitation radiation and for generating a response signal based on said detected physical response, said response signal being indicative of the degree of absorption of excitation radiation, and a control system.

Herein, said control system is configured to control the excitation radiation source to irradiate excitation radiation into the material to be absorbed therein, wherein the intensity of said excitation radiation is time-modulated, and wherein said excitation radiation comprises radiation of different analyte-characteristic-wavelengths that are irradiated one or both of simultaneously and sequentially, and to control the detection device to detect said physical response and to generate response signals indicative of the degree of absorption of said excitation radiation.

Moreover, said control system is further configured for controlling the apparatus to carry out a sequence of analyte-wavelength-specific measurements during said analyte measurement procedure while said thermal or pressure transmitting contact between the material and the measurement body is maintained, wherein in each analyte-wavelength-specific measurement, excitation radiation with an analyte-characteristic-wavelength selected from a predetermined set of analyte-characteristic-wavelengths is irradiated and a corresponding response signal is obtained, and wherein the control system is further configured for interspersing at least some of said analyte-wavelength-specific measurements with reference measurements, in which excitation radiation with a reference wavelength is irradiated and a corresponding response signal is obtained, wherein said reference wavelength is a wavelength different from any of said analyte-characteristic-wavelengths, and wherein said control system is configured for using response signals obtained for the reference measurements for one or more of calibrating an excitation radiation source for generating said excitation radiation, calibrating said detection device, recognizing a variation in the measurement conditions by comparing results of individual reference measurements, adapting the analyte measurement procedure with respect to one or more of the entire duration thereof, the absolute or relative duration of analyte-wavelength-specific measurements for a given analyte-characteristic-wavelength, or terminating and/or restarting the analyte measurement procedure, and adapting the analysis carried out in the analyzing step.

In a related embodiment, between at least 25%, preferably between at least 50% of each pairs of successive analyte-wavelength-specific measurements, a reference measurement is carried out.

In a preferred embodiment of the apparatus, said control system is configured to control the apparatus such that said reference measurements are carried out at an average rate of at least once every 5 seconds, preferably at least once per second, and most preferably at least 10 times per second.

In a preferred embodiment, said step of adapting the analysis carried out in the analyzing step based on the response signal obtained for the reference measurements comprises normalizing results of at least some of the analyte-wavelength-specific measurements based at least in part on the results of one or both of a preceding or succeeding reference measurement.

In an alternative embodiment of the apparatus, in addition or instead of the control system being configured for interspersing at least some of said analyte-wavelength-specific measurements with reference measurements, said control system is configured to control the apparatus such that during said analyte measurement procedure, a sequence of analyte-wavelength-specific measurements is carried out while maintaining said thermal or pressure transmitting contact between the material and the measurement body, wherein in each analyte-wavelength-specific measurement, excitation radiation with an analyte-characteristic-wavelength selected from a predetermined set of analyte-characteristic-wavelengths is irradiated and a corresponding response signal is obtained, and wherein the control system is further configured for carrying out a quality assessment based on the response signal associated with one or more analyte-characteristic-wavelengths, and to adjust, based on said quality assessment, the measurement time devoted to the corresponding one or more analyte-characteristic-wavelengths during the current analyte measurement procedure or one or more future analyte measurement procedures, or to adjust the relative weight associated with the corresponding analyte-wavelength-specific measurement in the analysis.

In a related embodiment, said control system is configured for controlling the apparatus to carry out the quality assessment during said analyte measurement procedure and to adjust the measurement time devoted to the corresponding one or more analyte-characteristic-wavelengths in real time during said analyte measurement procedure.

In a further related embodiment, said quality assessment is based, at least in part, on one or more of a signal-to-noise ratio of said response signal or a quantity derived therefrom, and the result of one or more reference measurements, in which excitation radiation with a reference wavelength is irradiated and a corresponding response signal is obtained, wherein said reference wavelength is a wavelength at which the absorption of said analyte is low.

In a further embodiment, the control system is configured to carry out a material status analyzing procedure, in which the present status of the material is analyzed based on one or more of one or more response signals established when the material is irradiated with excitation radiation at a wavelength different from said analyte-characteristic-wavelengths, one or more response signals established for excitation radiation with the same analyte-characteristic-wavelengths as used in the analyte measurement step, but for at least partially different intensity modulation frequencies of said excitation radiation than in the analyte measurement step, and one or more measurements related to the material status carried out with additional sensor equipment.

Moreover, the control system is configured for determining, based on a result of said material status analyzing procedure, at least one of a selection of analyte-characteristic-wavelengths used during said analyte measurement procedure, or relied on during said analysis, an absolute time or a relative time proportion of use of analyte-characteristic-wavelengths during said analyte measurement procedure, or a relative weight given to the wavelengths in the analysis, a selection of analyte-characteristic-wavelengths to be used simultaneously during said analyte measurement procedure, and a selection of one or more main frequencies of the modulation of said excitation radiation intensity to be used during said analyte measurement procedure.

In a preferred embodiment of the apparatus, said control system is configured to control the apparatus for carrying out a method according to any one of the above embodiments.

The control system may be embodied in hardware, software or both. In particular, the control system may comprise one or more computers, processors, microcontrollers, FPGAs ASICs and corresponding computer programs which when executed on the corresponding hardware provide the control functions described herein. In particular, the control system may be a distributed system, for example comprising several control units that are in data communication with each other, of which some may be provided in a housing of the apparatus, and others remote from the housing, but it can also be formed by a single control unit.

In a preferred embodiment of the apparatus said material is human tissue, in particular human skin, and said analyte is glucose present in the interstitial fluid thereof.

In a preferred embodiment of the apparatus, the control system is configured for carrying out the material status analyzing procedure interleavedly with the analyte measurement procedure, or less than five minutes, preferably less than three minutes, and most preferably less than one minute prior to the beginning of the analyte measurement procedure.

In a preferred embodiment of the apparatus, said material status comprises the presence and/or concentration of perturbing substances within said material that are different from said one or more analytes but exhibit significant absorptivity of excitation radiation at at least one of said analyte-characteristic-wavelengths, wherein in case said material status analyzing procedure yields a sufficiently high concentration of said perturbing substances, the control system is configured to avoid or suppress use of the at least one of said analyte-characteristic-wavelengths where said perturbing substances exhibit significant absorptivity.

In a preferred embodiment of the apparatus, said at least one main frequency of the modulation of said excitation radiation intensity to be used during said analyte measurement procedure comprise a first main modulation frequency and a second main modulation frequency, wherein said first main modulation frequency is sufficiently low such that the response signal reflects at least in part absorption of excitation radiation within the interstitial fluid, wherein the second main modulation frequency is higher than the first main modulation frequency.

In a preferred embodiment, said material status comprises the water content of the skin, and wherein the apparatus preferably further comprises a dedicated corneometric device for measuring the water content of the skin. In a related embodiment, in case a higher water content is determined in said material analyzing procedure, the control system is configured to preferentially use shorter wavelengths among a set of predetermined analyte-characteristic-wavelengths are preferentially in the analyte measurement procedure.

In a preferred embodiment of the apparatus, said control system is configured to adapt at least one of the one or more main frequencies of the modulation of said excitation radiation intensity used during said analyte measurement procedure to the water content determined in said material analyzing procedure in such a way that with all other characteristics of the material status the same, higher main frequencies of the modulation are chosen for higher water contents.

In a preferred embodiment of the apparatus, said material status comprises the thickness of the stratum corneum overlying the interstitial fluid. In a related embodiment, said control system is configured for assessing the thickness of the stratum corneum directly or indirectly based on response signals established for identical wavelengths of the excitation radiation but for different intensity modulation frequencies of said excitation radiation, wherein said wavelength is chosen to match an absorption band of a substance present with different concentrations in the stratum corneum and the interstitial fluid, respectively.

In a preferred embodiment, said control system is configured for adapting at least one of the one or more main frequencies of the modulation of said excitation radiation intensity used during said analyte measurement procedure to the thickness of the stratum corneum overlying the interstitial fluid determined in said material analyzing procedure in such a way that with all other characteristics of the material status the same, a lower main frequency of the modulation is chosen for higher stratum corneum thicknesses.

Preferably, said apparatus comprises a dedicated pH measuring device, and wherein said material status comprises the pH value of the skin. In a preferred embodiment, in case the pH value determined in said material analyzing procedure is found to be a lower value, with all other characteristics of the material status the same, the control system is configured to use analyte-characteristic-wavelengths overlapping with absorption bands of lactate less preferentially in the analyte measurement procedure than in case the pH is found to be a higher value.

In a preferred embodiment of the apparatus, the skin is skin at the fingertip of a human subject, and the apparatus further comprises a dedicated fingerprint sensor configured for estimating an average height of the epidermal ridges at the fingertip. Herein, the control system is preferably configured for adapting the power of the excitation radiation used in the analyte measurement procedure as a function of the average height of the epidermal ridges in such a manner that, with all other characteristics of the material status the same, the power of the excitation radiation used in the analyte measurement procedure is increased for higher average epidermal ridges.

In a preferred embodiment, the apparatus may further comprise a temperature sensor for measuring the temperature of the skin.

In a preferred embodiment of the apparatus, the control system is configured to control the apparatus to provide a time modulation of said intensity of said excitation radiation such that the envelope of the intensity is asymmetrical in that the proportion of time during which the envelope assumes 50% or more of the average intensity is less than 50%, preferably less than 46% and most preferably less than 43% of the total time. However, the proportion of time during which the envelope is less than 50% should not be chosen too low, and is preferably at least 20%, more preferably at least 30%.

In a preferred embodiment of the apparatus, the control system is configured to control the apparatus to provide a time modulation of said intensity of said excitation radiation such that the envelope of the intensity follows a periodically repeating pattern, wherein said pattern includes a high intensity time portion including more than 80% of the intensity-time-integral and a low intensity time portion including less than 20% of the intensity-time-integral of the pattern, wherein the ratio of the durations of the high and low intensity time portions is less than 0.9, preferably less than 0.8, and most preferably less than 0.7. However, in preferred embodiments, this ratio should be at least 0.4, and preferably at least 0.5.

In a preferred embodiment of the apparatus, the control system is configured to control the apparatus to provide a time modulation of said intensity of said excitation radiation such that the envelope of the intensity is approximately harmonic such that in a Fourier decomposition of the intensity of the excitation radiation, of the total intensity associated with the dominant frequency and the $1^{st}$ to $9^{th}$ harmonics, at least 95% is associated with the dominant frequency and at least 97%, preferably at least 98% is associated with the dominant frequency and first harmonic.

In a preferred embodiment of the apparatus, said detection device comprises a light source for generating a detection light beam travelling through at least a portion of said measurement body or a component included in said measurement body,

- said physical response of the measurement body to heat or pressure waves received from said material upon absorption of said excitation radiation is a local change in the refractive index of said measurement body or said component, and
- said detection device is configured for detecting one of a change in the light path or a change in the phase of detection beam due to said change in refractive index change in light path or phase of the detection beam.

In a related embodiment, said measurement body is transparent for said detection light beam, said detection light beam is directed to be totally or partially reflected at a surface of said measurement body that is in thermal contact or pressure transmitting contact with said material, and wherein said detection device comprises a photodetector, in particular a position sensitive photodetector, capable of detecting a degree of deflection of said detection light beam due to said local change in refractive index.

In an alternative embodiment of the apparatus, said detection device comprises an interferometric device allowing for assessing said change in phase of the detection beam and generating a response signal indicative of said change in phase.

In a preferred embodiment of the apparatus, said measurement body or a component in said measurement body has electrical properties that change in response to a local change in temperature or a change in pressure associated therewith, and wherein said detection device comprises electrodes for capturing electrical signals representing said electrical properties.

In a preferred embodiment of the apparatus, said excitation radiation source comprises an array of lasers, in particular quantum cascade lasers, each having a dedicated wavelength.

In a preferred embodiment of the apparatus, said excitation radiation source comprises at least one tunable laser, in particular at least one tunable quantum cascade laser.

In a preferred embodiment of the apparatus, some or all of said excitation wavelengths are in a range of 5 μm to 13 μm, preferably 8 μm to 11 μm. In alternative embodiments, some or all of said excitation wavelengths are in a range of 3 μm to 5 μm.

In preferred embodiments, the method comprises, in addition to or instead of said material status analyzing procedure, a step of receiving user-related input allowing for optimizing one or both of the analyte measurement procedure and the analysis carried out in the analyzing step.

Similarly, the apparatus may, in addition to or instead of being further configured to carry out said material status analyzing procedure, comprise an input interface for receiving user-related input and configured for using this input for optimizing one or both of the analyte measurement procedure and the analysis carried out in the analyzing step.

In some embodiments, where said step of receiving user-related input is provided in addition to said material status analyzing procedure, based on both, a result of said material status analyzing procedure and said user-related input, at least one of

- a selection of analyte-characteristic-wavelengths used during said analyte measurement procedure, or relied on during said analysis,
- an absolute time or a relative time proportion of use of analyte-characteristic-wavelengths during said analyte measurement procedure, or a relative weight given to the wavelengths in the analysis,
- a selection of analyte-characteristic-wavelengths to be used simultaneously during said analyte measurement procedure, and
- a selection of one or more main frequencies of the modulation of said excitation radiation intensity to be used during said analyte measurement procedure is determined.

The user input could for example specify certain characteristics or conditions of a person being subjected to a glucose measurement in the manner described above.

For example, characteristics of the person could be

- the color of the skin of the person (e.g. whether the user's skin is of light or dark color),
- information related to the weight of the person, such as body mass index or the like,
- whether or not the person suffers from chronic diseases, and if yes, which ones, and in particular, whether the person suffers from diabetes,
- the age of the person,
- the profession of the person,

- hobbies, including typical sport or physical exercises,
- whether the person has typically high or low blood pressure.

All of these characteristics may have an impact on the optimum way the analyte measurement procedure is carried out and/or on the optimum way the analysis is carried out.

In addition or alternatively to the characteristics, the user-related input could also comprise information related to the condition of the user. Examples for the condition of the person can be

- whether the person is currently sweating,
- whether the person has a cold and/or a fever, or
- whether the person is feeling cold,
- whether the person has recently drunken water or other drinks,
- whether the person is currently on a diet,
- whether the person feels stressed or under time pressure.

One difference between user-related "characteristics" and "conditions" is that conditions may change more frequently, and that input of user-related conditions may therefore be requested more often, for example any time a measurement is carried out, or at least once for all measurements carried out during a same time span, for example during the same day. In contrast to this, the characteristics need to be inputted less frequently.

In preferred embodiments, based on the user-related characteristics or conditions received by input, a protocol for carrying out the analyte measurement procedure may be generated or selected from a number of predetermined protocols.

Different protocols, selected or generated based on the characteristics/conditions of the user, may differ with respect to one or more of

- a selection of analyte-characteristic-wavelengths used during the analyte measurement procedure, or relied on during the analysis;
- an absolute time or a relative time proportion of use of analyte-characteristic-wavelengths during said analyte measurement procedure, an individual excitation radiation intensity, or a relative weight given to the wavelengths in the analysis,
- a selection of analyte-characteristic-wavelengths to be used simultaneously during such analyte measurement procedure, and
- a selection of one or more main frequencies of the modulation and of said excitation radiation intensity to be used during said analyte measurement procedure.

In some embodiments, there is a number of predetermined protocols of carrying out the analyte measurement procedure, wherein these protocols may have been previously empirically determined to work particularly well for the given characteristics and/or conditions. These predetermined protocols could be used instead of the material status analyzing procedure described above. In other embodiments, these protocols can be used as a starting point and then be refined based on the results of the material status analyzing procedure described above.

In addition, or alternatively, as mentioned before, the user-related characteristics and/or conditions received by input can also be used for adapting the analysis carried out in the analyzing step. For example, the analysis may comprise one or more algorithms that translate the aforementioned response signals into an estimate of a glucose concentration. The inventors have noticed that the accuracy of such algorithms can be increased if they are specifically adapted to, or take account of, the aforementioned characteristics and/or conditions.

Accordingly, in a preferred embodiment, said analyzing step is carried out using one or more algorithms, said one or more algorithms being selected or adapted according to said user-related characteristics and/or conditions.

For example, the analyzing step may comprise various machine learning based algorithms to choose from, each of which having been trained on data associated with specific selections of some or all of the aforementioned characteristics or conditions. Then, based on the input of user-related characteristics/conditions, an appropriate one of these algorithms can be selected for use in the analyzing step, and can therefore make particularly precise estimates based on response signals recorded for these types of characteristics and conditions. Herein, an "appropriate one" (or most appropriate one) of these algorithms may be the algorithm in which the training data is close to (or the closest to) the user-related characteristics and/or conditions.

In other embodiments, the algorithms used in the analysis may comprise one or more adjustable parameters, and said method comprises a step of adjusting said one or more adjustable parameters based on the aforementioned characteristics and/or conditions.

With regard to the apparatus, the aforementioned control system of the apparatus may be configured for carrying out each of the methods summarized above that rely on the input of said user-related characteristics and/or conditions.

In particular, said control system may be configured for carrying out said analyzing step, and may be further configured for adapting this analyzing step based on the user-related characteristics and/or conditions.

Preferably, the control system comprises a memory storing various machine learning based algorithms to choose from, each of which having been trained on data associated with specific selections of some or all of the aforementioned characteristics or conditions. The control system may then be further configured for selecting, based on the input of user-related characteristics/conditions, an appropriate one of these algorithms for use in the analyzing step.

In addition or alternatively, the control system comprises a memory storing one or more algorithms for use in the analysis, said one or more algorithms comprising one or more adjustable parameters, wherein said control system is further configured for adjusting said one or more adjustable parameters based on the aforementioned characteristics and/or conditions.

In preferred embodiments, the user-related input is received by user input. The apparatus may comprise a user interface for inputting such information regarding the characteristics or condition of the user.

In preferred embodiments, the user interface is provided by a touch display device associated with the apparatus.

In each of the embodiments described above, a camera may be provided for recording images of the material (in particular the skin) in the region where the excitation radiation is to be irradiated into the material (skin). In preferred embodiments, the camera is an infrared camera for recording infrared images. These images can be used for several purposes. For example, using the camera image, it can be determined whether the apparatus is properly positioned with respect to the material, and in particular, with the skin.

In preferred embodiments, the method comprises a step of identifying, within the image, the location where the excitation radiation beam will be irradiated into the material. For example, with specific reference to analysis of the skin, the method may comprise a step of determining whether for the given position of the apparatus relative to the skin, the excitation radiation will be irradiated into the skin at a suitable location. A suitable location would for example be a location where the skin is relatively smooth. Further criteria for a "suitable location" would be the absence of wrinkles, the absence of hairs, the absence of scars or the absence of moles.

This is particularly important in preferred embodiments of the method, where places other than the finger-tip are used for the measurement, in particular the skin on the underside of the wrist. Based on a known relative position of the camera with respect to the excitation light source or at least with respect to the light path of the excitation light beam generated thereby, the location where the excitation radiation enters the skin can be precisely discerned within the image. If a fingertip is used for the measurement, a suitable location for the excitation radiation to be radiated into the skin would be at an epidermal ridge thereof, where the optical coupling is found to be better than in a groove between two adjacent epidermal ridges.

The determining of whether for a current position of the apparatus relative to the skin, the excitation radiation will be radiated into the skin at a suitable location can be made using a corresponding algorithm for analyzing the relevant portion of the image with respect to one or more of the above criteria. If it is determined that the location is not suitable (with respect to one or more predetermined criteria), the user may be prompted via an output interface to position the apparatus with respect to the skin anew. This may be repeated until a suitable location has been established. In preferred embodiments, the output interface may be a display, in particular a touch display. In addition or alternatively, the output interface may comprise an acoustic output device.

In preferred embodiments, the method in addition or alternatively comprises a step of using camera images of the material (in particular the skin) for monitoring whether the apparatus (and in particular, the measurement body) is moved with respect to the material (skin) during the analyte measurement procedure. Absence of such movement is referred to as "positional stability" herein. The positional stability can for example be assessed by comparing consecutively recorded images of the material (skin), wherein deviations between consecutive images are indicative of a relative movement of the measurement body with respect to the material (skin), whereas lack of such deviations are indicative of positional stability.

In preferred embodiments, information with respect to a suitable location of the excitation radiation and/or positional stability or relative movement can be exploited in a similar manner as in the "quality assessment" described above, and/or may be combined with it. Note that the quality assessment described above was based on the response signals, not on camera images. However, this quality assessment can also additionally include information regarding the suitability of the location of the excitation radiation and/or positional stability.

In particular, based on the detected positional stability, the measurement time devoted to one or more analyte-characteristic-wavelengths during the current analyte measurement procedure may be adjusted, or the relative weight associated with the corresponding analyte-wavelength-specific measurement in the analysis may be adjusted. For example, if it is determined that the change in position occurred during the measurement of a given analyte-characteristic wavelength, the measurement time devoted to this wavelength may be increased, to compensate for loss of reliable measurement data during the relative movement. In the alternative, the relative weight associated with the corresponding analyte-wavelength-specific measurement in the analysis may be reduced, to account for expected inaccuracy of the corresponding measurement. In addition or alternatively, based on the positional stability monitored, the measurement can be terminated and started anew. For example, if the change in position occurred shortly after the beginning of the measurement, where not much useful measurement data has yet been accumulated, it may be more advisable to discard the entire measurement and start anew. A similar situation may arise if it is determined that a relative motion of the apparatus with respect to the material (skin) has led to a situation in which the location of the excitation radiation is no longer suitable. In this case the method may comprise a step of terminating the measurement, prompting the user to relocate the apparatus and to start anew.

In preferred embodiments, the user is informed if the measurement is terminated due to a relative movement between the measurement body and the skin, to increase the user's awareness and to ensure a positional stability in the next attempt of the analyte measurement procedure. In preferred embodiments, this information is conveyed via an acoustic signal, which captures the user's immediate attention, as compared to an output via a display only In preferred embodiments, the control system is configured for carrying out some or all of the described embodiments related to the method of identifying suitable locations for the irradiation with excitation radiation and of the method of monitoring movement of the apparatus relative to the material (skin). In particular, the control system may be configured for one or more of

- controlling said camera to record an image of the material (in particular the skin) in the region where the excitation radiation is to be irradiated into the material (skin),
- identifying, within the image, the location where the excitation radiation beam will be irradiated into the material,
- determining whether for the given position of the apparatus relative to the skin, the excitation radiation will be irradiated into the skin at a suitable location, in particular based on criteria such as the absence of wrinkles, the absence of hairs, the absence of scars or the absence of moles, in particular using an algorithm stored in a memory associated with the control system,
- prompting a user via an output interface to position the apparatus with respect to the skin anew, if the control system has determined that the location is not suitable (with respect to one or more predetermined criteria), in particular by means of a display, such as a touch display and/or by means of an acoustic output device,
- monitoring whether the apparatus (and in particular, the measurement body) is moved with respect to the material (skin) during the analyte measurement procedure, in particular by
- comparing consecutively recorded images of the material (skin),
- adjusting, based on the detected positional stability, the measurement time devoted to one or more analyte-characteristic-wavelengths during the current analyte measurement procedure, or the relative weight associated with the corresponding analyte-wavelength-specific measurement in the analysis and/or terminating, based on the positional stability monitored, the measurement and controlling the measurement to start anew, informing a user if the measurement is terminated due to a relative movement between the measurement body and the skin.

In preferred embodiments, the measurement body is transparent for the imaging wavelength of the camera, and the camera is arranged such as to record images through the measurement body.

The camera images can also be used for identifying skin patterns, such as fingerprints, but also patterns of the skin at flat skin regions such as on the underside of the wrist. These images can be stored, and can be used to ensure that a same location for the user measurement is used that has previously been chosen to thereby allow for comparing measurement results.

A further aspect of the invention relates to a method of analyzing a material comprising at least one analyte, said method comprising an analyte measurement procedure, in which the material is brought in thermal contact or pressure transmitting contact with a measurement body, said thermal or pressure transmitting contact permitting heat or pressure waves generated by absorption of excitation radiation in the material to be transferred to said measurement body, excitation radiation is irradiated into the material to be absorbed therein, wherein the intensity of said excitation radiation is time-modulated, and wherein said excitation radiation comprises radiation of different analyte-characteristic-wavelengths that are irradiated one or both of simultaneously and sequentially, and a physical response of the measurement body, or of a component included therein, to heat or pressure waves received from said material upon absorption of said excitation radiation is detected using a detection device which generates a response signal based on said detected physical response, said response signal being indicative of a degree of absorption of excitation radiation, wherein the method further comprises an analyzing step, in which said analyzing is carried out based, at least in part, on said response signal, wherein during said analyte measurement procedure, a sequence of analyte-wavelength-specific measurements is carried out while maintaining said thermal or pressure transmitting contact between the material and the measurement body, wherein in each analyte-wavelength-specific measurement, excitation radiation with an analyte-characteristic-wavelength selected from a predetermined set of analyte-characteristic-wavelengths is irradiated and a corresponding response signal is obtained, wherein prior to or during said analyte measurement procedure, one or more images of said material in the region where the excitation radiation is to be irradiated into the material are recorded, and the method comprises one or both of a step of determining, based on said one or more images, whether for the given position of the measurement body relative to the material, the excitation radiation will be irradiated into the material at a suitable location for carrying out the analyte measurement procedure, and a step of using camera images of the material for monitoring whether the the measurement body is moved with respect to the material during the analyte measurement procedure.

In preferred embodiments of said method, said material is human tissue, in particular human skin, and said analyte is glucose present in an interstitial fluid thereof.

In a preferred embodiment of the method, the skin is formed by skin at the underside of the wrist of a person. In a preferred embodiment, said suitable location is a location where the skin is one or more of smooth, free or almost free of wrinkles, free or almost free of hairs, free of scars, or free of moles.

In a preferred embodiment of the method, said skin is formed by skin on a fingertip, and said suitable location is a location at an epidermal ridge.

In a preferred embodiment of the method, if it is determined that the location is not suitable (e.g. with respect to one or more predetermined criteria), a user is prompted via an output interface to position the measurement body with respect to the skin anew. Herein, the output interface may be a display, in particular a touch display. In addition or alternatively, the output interface may comprise an acoustic output device.

In preferred embodiments of the method, said step of using camera images of the material, in particular skin, for monitoring whether the measurement body is moved with respect to the material (skin) during the analyte measurement procedure comprises comparing consecutively recorded images of the material (skin). Herein, deviations between consecutive images are indicative of a relative movement of the measurement body with respect to the material (skin), whereas lack of such deviations are indicative of positional stability.

In preferred embodiments of the method, based on the detected positional stability, the measurement time devoted to one or more analyte-characteristic-wavelengths during the current analyte measurement procedure is adjusted, or the relative weight associated with the corresponding analyte-wavelength-specific measurement in the analysis is adjusted. In addition or alternatively, based on the positional stability monitored, the measurement can be terminated and started anew.

In preferred embodiments of the method, the user is informed if the measurement is terminated due to a relative movement between the measurement body and the skin, to increase the user's awareness and to ensure a positional stability in the next attempt of the analyte measurement procedure. In preferred embodiments, this information is conveyed via an acoustic signal, which captures the user's immediate attention, as compared to an output via a display only The further aspect of the invention further relates to an apparatus for analyzing a material comprising at least one analyte, said apparatus comprising a measurement body having a contact surface suitable to be brought in thermal contact or pressure transmitting contact with said material, said thermal or pressure transmitting contact permitting heat or pressure waves generated by absorption of excitation radiation in the material to be transferred to said measurement body, an excitation radiation source configured for irradiating excitation radiation into the material to be absorbed therein, a detection device for detecting a physical response of the measurement body, or of a component included therein, to heat or pressure waves received from said material upon absorption of said excitation radiation and for generating a response signal based on said detected physical response, said response signal being indicative of a degree of absorption of excitation radiation, a camera and a control system, wherein said control system is configured to control the excitation radiation source (26) to irradiate excitation radiation into the material (12) to be absorbed therein, wherein the intensity of said excitation radiation is time-modulated, and wherein said excitation radiation comprises radiation of different analyte-characteristic-wavelengths that are irradiated one or both of simultaneously and sequentially, and to control the detection device to detect said physical response and to generate response signals indicative of the degree of absorption of said excitation radiation (18), wherein said control system is configured to control the apparatus such that during said analyte measurement procedure (78), a sequence of analyte-wavelength-specific measurements is carried out while maintaining said thermal or pressure transmitting contact between the material (12) and the measurement body (16), wherein in each analyte-wavelength-specific measurement, excitation radiation (18) with an analyte-characteristic-wavelength selected from a predetermined set of analyte-characteristic-wavelengths is irradiated and a corresponding response signal is obtained, wherein said control system is further configured for controlling said camera, prior to or during said analyte measurement procedure, to record one or more images of said material in the region where the excitation radiation is to be irradiated into the material, and as further configured for carrying out one or both of a step of determining, based on said one or more images, whether for the given position of the measurement body relative to the material, the excitation radiation will be irradiated into the material at a suitable location for carrying out the analyte measurement procedure, and a step of using camera images of the material for monitoring whether the the measurement body is moved with respect to the material during the analyte measurement procedure.

In preferred embodiments, the control system of the apparatus according to said further aspect is configured for carrying out some or all of the described embodiments related to the method of identifying suitable locations for the irradiation with excitation radiation and of the method of monitoring movement of the apparatus relative to the material (skin). In particular, the control system may be configured for one or more of controlling said camera to record an image of the material (in particular the skin) in the region where the excitation radiation is to be irradiated into the material (skin), identifying, within the image, the location where the excitation radiation beam will be irradiated into the material, determining whether for the given position of the apparatus relative to the skin, the excitation radiation will be irradiated into the skin at a suitable location, in particular based on criteria such as the absence of wrinkles, the absence of hairs, the absence of scars or the absence of moles, in particular using an algorithm stored in a memory associated with the control system, prompting a user via an output interface to position the apparatus with respect to the skin anew, if the control system has determined that the location is not suitable (with respect to one or more predetermined criteria), in particular by means of a display, such as a touch display and/or by means of an acoustic output device, monitoring whether the apparatus (and in particular, the measurement body) is moved with respect to the material (skin) during the analyte measurement procedure, in particular by comparing consecutively recorded images of the material (skin), adjusting, based on the detected positional stability, the measurement time devoted to one or more analyte-characteristic-wavelengths during the current analyte measurement procedure, or the relative weight associated with the corresponding analyte-wavelength-specific measurement in the analysis and/or terminating, based on the positional stability monitored, the measurement and controlling the measurement to start anew, and/or informing a user if the measurement is terminated due to a relative movement between the measurement body and the skin.

SHORT DESCRIPTION OF THE FIGURES

DESCRIPTION OF THE PREFERRED EMBODIMENTS

It is to be understood that both the foregoing general description and the following description are exemplary and explanatory only and are not restrictive of the methods and devices described herein. In this application, the use of the singular may include the plural unless specifically state otherwise. Also, the use of "or" means "and/or" where applicable or unless stated otherwise. Those of ordinary skill in the art will realize that the following description is illustrative only and is not intended to be in any way limiting. Other embodiments will readily suggest themselves to such skilled persons having the benefit of this disclosure. Reference will now be made in detail to various implementations of the example embodiments as illustrated in the accompanying drawings. The same reference signs will be used to the extent possible throughout the drawings and the following description to refer to the same or like items.

Figure 1:
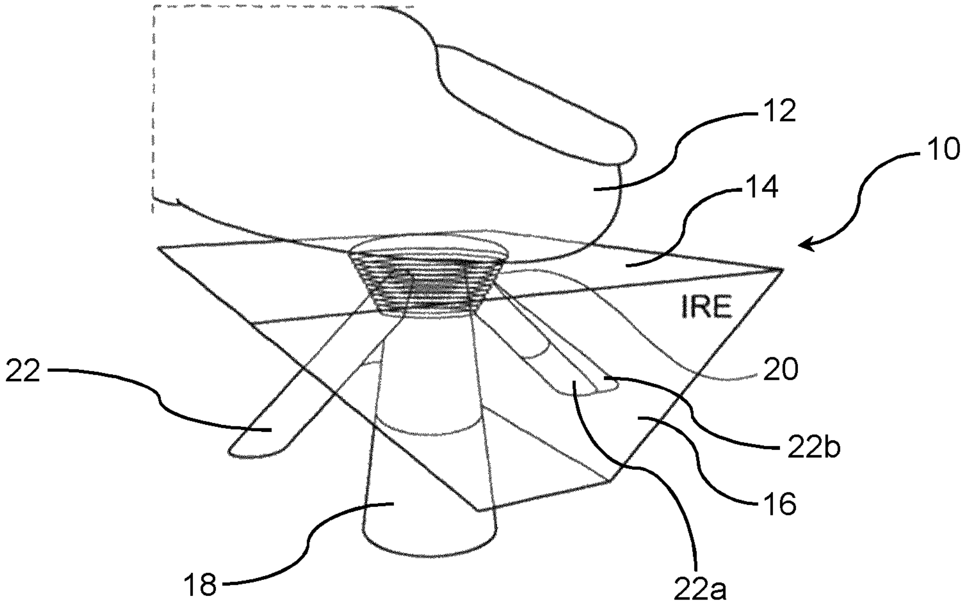
FIG. 1 is a schematic illustration of the measurement principle underlying one embodiment of the invention.

FIG. 1 is a schematic illustration of the measurement principle underlying the analyte measurement procedure summarized above and described in more detail in the following. While the method and apparatus of the invention are suitable for analyzing various materials comprising at least one analyte, the following description will focus on specific embodiments, where the material is the skin of a patient and the analyte is glucose within the interstitial fluid of the skin. It is to be understood that all details and explanations given in the following with specific reference to glucose measurement are considered in relation to other materials and analytes as well, where applicable, without explicit mention in the following.

Figure 2:
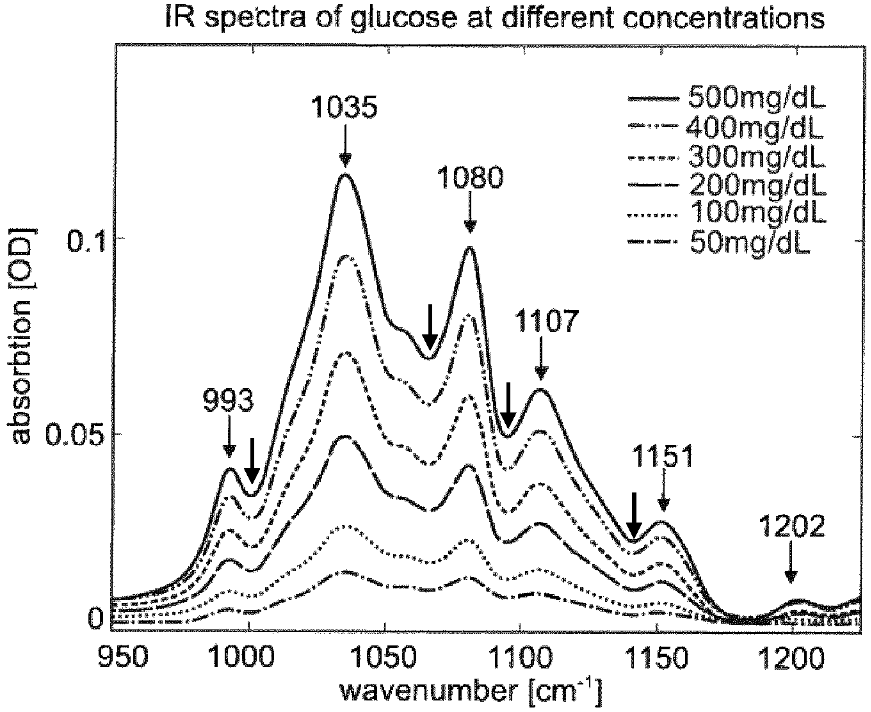
FIG. 2 shows the absorption spectrum of the glucose in water, with the water background subtracted.

In the illustration of FIG. 1, a fingertip 12 of a user is brought in thermal contact with a contact surface 14 of a measurement body 16. In an alternative implementation, which is not shown, the fingertip may be coupled acoustically to the measurement body through an acoustic cell which may include a hollow space filled with a liquid or gas allowing for a transfer of pressure waves to the measurement body. An excitation beam 18 is irradiated to the measurement body 16 through air or through a waveguide (not shown) and then through the measurement body 16 and into the skin at the fingertip 12. In order to determine the concentration of the glucose in the skin, in particular in the interstitial fluid of the skin, various wavelengths of the excitation radiation 18 are chosen one after the other or at least partially at the same time for absorption measurement, such that from the measured absorption values the concentration of the glucose can be determined. In FIG. 2, absorption spectra are shown for different concentrations of glucose in water, wherein the contribution of the absorption by water has been subtracted. As is seen therein, the glucose molecule has several characteristic absorption peaks in the mid infrared region at wave numbers ranging between 993 $cm^{-1}$ and 1202 $cm^{-1}$, corresponding to wavelengths ranging from 10.07 μm to 8.32 μm, respectively. In between adjacent absorption peaks, local absorption minima are seen, which are indicated by vertical arrows without wave numbers in FIG. 2. As is apparent from FIG. 2, particularly the difference in absorption at the absorption peaks and the local absorption minima are characteristic for the glucose concentration. Accordingly, in order to be able to determine the glucose concentration, it is preferable to measure the absorption at some or all of the absorption peaks and at some or all of the local absorption minima and potentially also at some point between the maxima and minima. These wavelengths are referred to as a "analyte(glucose)-characteristic-wavelengths" herein. Note, however, that the absorptivity at the lowest local minimum at 1140 cm-1 is still 18% of the absorptivity at the highest peak at 1035 cm-1 in the relevant part of the spectrum. Accordingly, the absorption at any of these wavelengths will noticeably depend on the concentration of the glucose, such that these wavelengths are characteristic for the glucose, i. e. "glucose-characteristic wavelengths". In contrast to this, at about 1180 cm-1, the absorptivity is practically zero, and hence a global rather than a local minimum, and this wavelength is obviously a not characteristic for the glucose. While wavelengths exactly at the absorption peaks or local absorption minima are the preferred choices for the glucose-characteristic wavelengths, wavelengths close to the peaks/local minima but in an individually defined distance from them may also be used. Accordingly, as understood herein, "analyte-characteristic-wavelengths" are also wavelengths where the difference in absorption to that at the closest absorption peak or the closest local absorption minimum is less than 30%, preferably less than 20% of the difference in absorption between the closest absorption peak and closest local absorption minimum.

The intensity of the excitation beam 18 is time modulated with a certain frequency f, such that the excitation radiation, in this case excitation light has alternating intervals of high intensity and low or even vanishing intensity. Without wishing to limit the modulation to any particular waveform, high intensity intervals are referred to as "excitation light pulses" in the following. During the excitation light pulses, excitation light having the glucose-characteristic-wavelength will be absorbed, such that the radiation energy will be converted to heat. Since the glucose molecules relax from the excited state within approximately $10^{-12}$ s, the generation of a corresponding heat pulse and/or pressure wave can be regarded as occurring instantaneously for all practical purposes.

Accordingly, along with the excitation light pulses, local heat pulses are generated at the absorption site, leading to a temperature field that varies as a function of space and time and that could be referred to as a thermal wave. As was explained above, the term thermal "wave" is somewhat misleading, since the travel of heat through the material is not governed by a wave equation, but by a diffusion equation instead. However, the notion of a "heat wave" is correct at least to the extent that heat pulses propagate from within the skin to the surface 14 of the measurement body 16 and into the measurement body 16 similarly to what one is used to from wave propagation. A thermal gradient 20 that is caused by such a heat pulse is schematically shown in FIG. 1.

Figure 12:
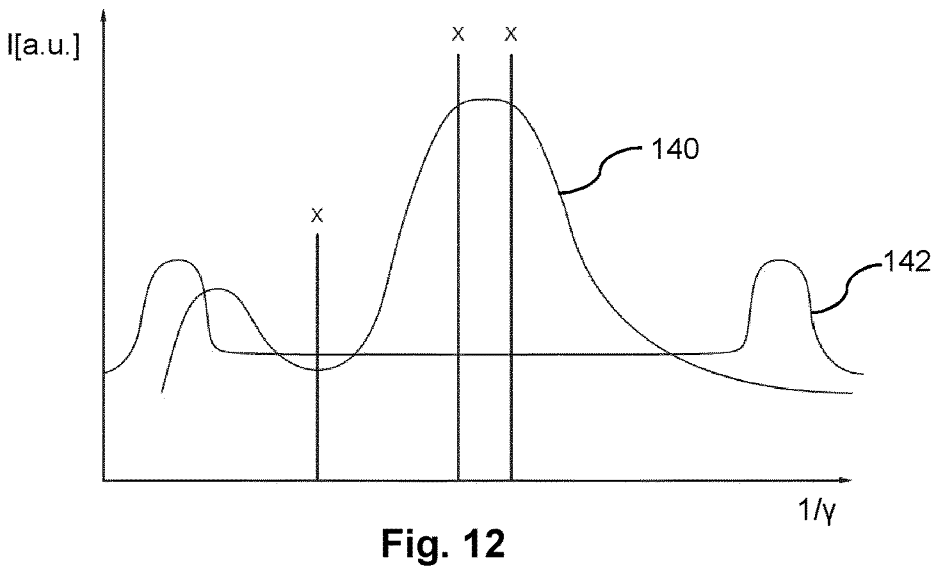
FIG. 12 is a schematic illustration of absorption spectra of the analyte and the disturbing substance of FIG. 11, but with a high concentration of the disturbing substance, as well as correspondingly selected excitation radiation wavelengths.

The heat received by the measurement body 16 from the skin of the FIG. 12 causes a physical response that can be detected with one of various possible detection devices which are devised for generating a response signal based on the physical response, wherein this response signal is indicative of the degree of absorption of the excitation light. Various ways of detecting the physical response and generating suitable response signals will be described below.

However, irrespective of the precise way of detecting the physical response, it is worth noting that the maximum depth underneath the surface of the skin in which the absorption can be detected by means of heat pulses travelling to the measurement body 16 is found to be limited to a good approximation by the thermal diffusion length $\mu_t$ of the skin, which is defined as $$\mu t(f) = \sqrt{\frac{kt}{\rho \cdot Cp \cdot 2f}}$$

and which depends on the density ρ, the specific heat capacity $C_p$, and the thermal conductivity $k_t$ of the material as well as on the modulation frequency f of the excitation light. In other words, by selecting the modulation frequency f, a depth can be defined up to which any absorption of the excitation light is reflected in the heat pulses received at the measurement body 16.

With reference again to FIG. 1, in the embodiment shown, the physical response to the absorption heat received from the skin is a change in refractive index in an area close to the surface 14 of the measurement body 16 where the heat gradient 20 is transiently formed. This local change in refractive index forms what could be regarded as a thermal lens that can be detected by means of a detection light beam 22. The detection beam 22 is passing through the thermal lens or heat gradient region and then reflected at the interface of the measurement body 16 and the skin of the FIG. 12. Whenever a heat pulse is received from the skin, a local change in refractive index occurs, and this leads to a deflection of the detection beam 22 by the interaction with the material of the measurement body in the region of the thermal lens. In FIG. 1, reference sign 22*b* corresponds to the non-deflected detection beam 22, whereas reference sign 22*a* corresponds to the detection beam when it is deflected due to the thermal lens formed in the heat gradient region 20. This deflection can be measured and forms an example of the aforementioned response signal. The degree of the deflection is indicative of the amount of heat received, and hence the degree of absorption of the excitation light 18 in the skin of the finger 12.

Figure 3:
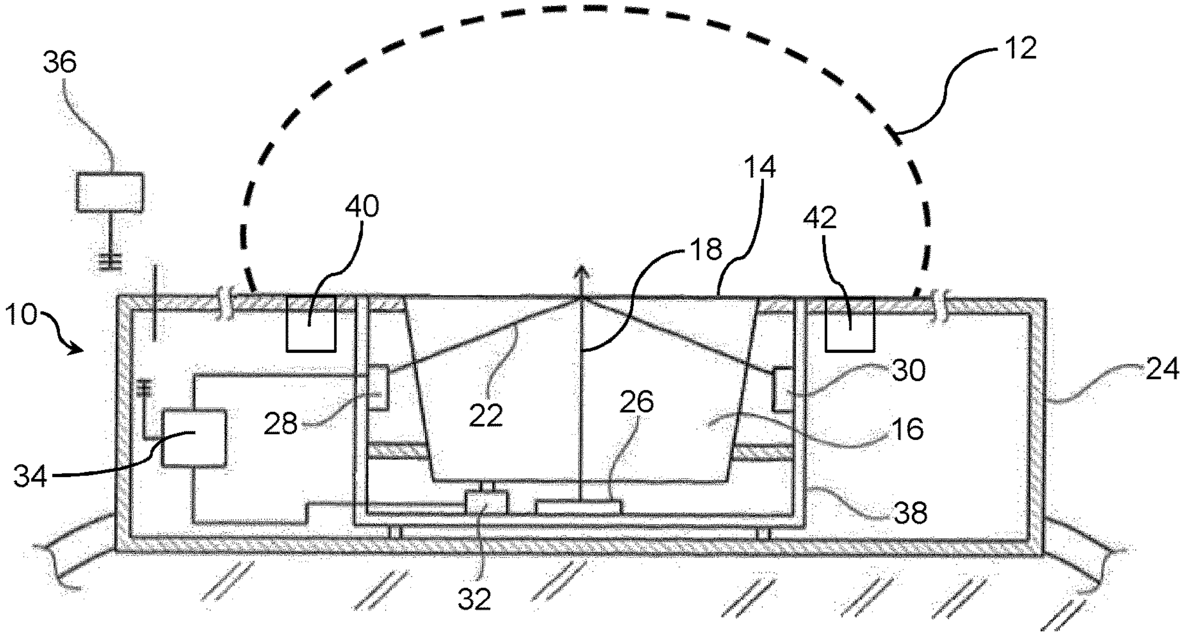
FIG. 3 is a schematic sectional view of an apparatus suitable for carrying out embodiments of the invention relying on response signals based on a deflection of a detection light beam.

FIG. 3 shows a more detailed sectional view of an apparatus 10 that relies on the measurement principle as illustrated with reference to FIG. 1. The apparatus 10 comprises a housing 24 which includes the measurement body 16, having a top surface (contact surface) 14 on which a finger 12 rests. Within the housing 24, an excitation light source 26 is provided, which generates the excitation light beam 18. In the embodiment shown, the excitation light source 26 comprises an array of quantum cascade lasers each having a dedicated wavelength. For example, the array of quantum cascade lasers could include individual quantum cascade laser elements with wavelengths corresponding to the absorption peaks and local minima shown in FIG. 2 (i.e. the glucose-characteristic-wavelengths), as well as other wavelengths that can be used for reference measurements, or for detecting other substances that could be disturbing to the measurement of the glucose, for example lactate or albumin.

The apparatus 10 further comprises a light source 28, for example a laser, for emitting the detection beam 22, as well as a position-sensitive detector 30 which allows for detecting the deflection of the detection beam 22. The measurement body 16 in this case is transparent for both, the excitation light beam 18 as well as the detection light beam 22. In addition, a camera 32 or another imaging device is provided that allows for taking images of the contact surface 14 of the optical medium 16, to thereby record a fingerprint of the finger 12 resting on the contact surface 14. This fingerprint can be processed by a control unit 34 such as to identify a user via his or her fingerprint. The control unit 34 also serves for controlling the light sources 26 and 28 for the excitation light and the detection light, respectively, as well as the sensor 30. The control unit 34 is also in wireless connection with an external data processing device 36 to exchange data. For example, via the wireless connection, user-specific calibration data can be retrieved by the control unit 34 for the user that is identified via the fingerprint. The control unit 34 and the external data processing device 36 together form an example of a "control system" as referred to above. The control system can be comprised by one or more processors, microcontrollers, computers, ASICs, FPGAs, or the like. The control system may be distributed, as indicated in FIG. 3, with various components in data communication with each other, or could be formed by a single control unit, such as the control unit 34, which would be devised for all of the control functionalities described herein. The control system may be generally embodied in hardware, in software, or a combination of both.

As is further seen in FIG. 3, the excitation and detection light sources 26 and 28, as well as the position sensitive detector 30 are all attached to a common carrier structure 38. This means that these components can be preassembled with precision on this structure 38, such that they do not need to be individually adjusted or calibrated when assembling the apparatus 10.

In addition, the apparatus 10 comprises a corneometric device 40 that allows for measuring the water content of the skin. Corneometric devices for measuring the water content in the upper layer of the skin are per se known in the art and need not be described in detail here. For example, known corneometric devices measure the impedance, in particular capacitive impedance of the skin using two interdigital electrodes to which an AC voltage is applied. The corneometric device 40 of FIG. 3 is in contact with the fingertip 12 when the latter rests on the contact surface 14 of the measurement body 16. The corneometric device 40 is an example of the aforementioned "additional sensor equipment", i.e. a sensor that is per se unrelated to the measurement apparatus for measuring the analyte absorption.

The apparatus also comprises a pH-sensor 42 for measuring the pH value of the skin. pH sensors for measuring the pH value on surfaces, including those of the skin are per se known from prior art and need not be described in detail herein. pH sensors for measuring the pH value of the skin are commercially available for medical but also for cosmetic purposes.

Figure 4:
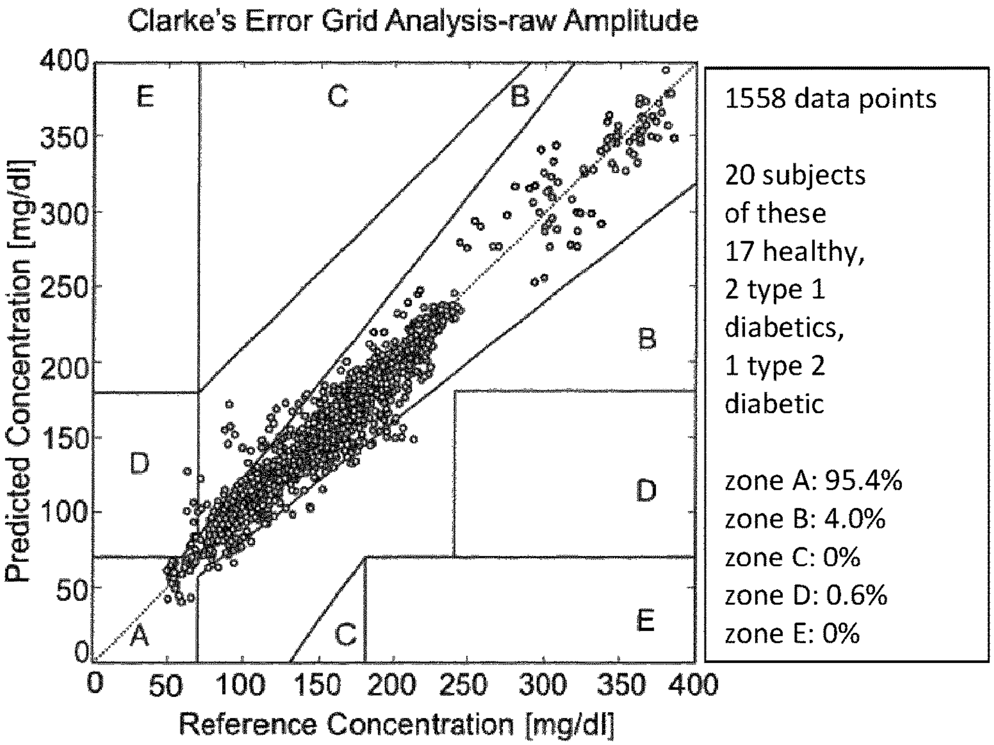
FIG. 4 shows results of a Clarke's error grid analysis obtained with an apparatus of the type shown in FIG. 3.

FIG. 4 shows results of a Clarke's error grid analysis obtained with an apparatus of the type shown in FIG. 3, illustrating that with the measurement procedure described with reference to FIG. 1 to 3, indeed very reliable blood sugar concentrations can be measured in a purely non-invasive manner. The data shown in FIG. 4 are taken from WO 2017/09782 A1 and do not yet reflect improvements of the present invention. The present invention allows for improving the reliability of the method even further, and to reduce the measurement times needed for it.

Figure 5:
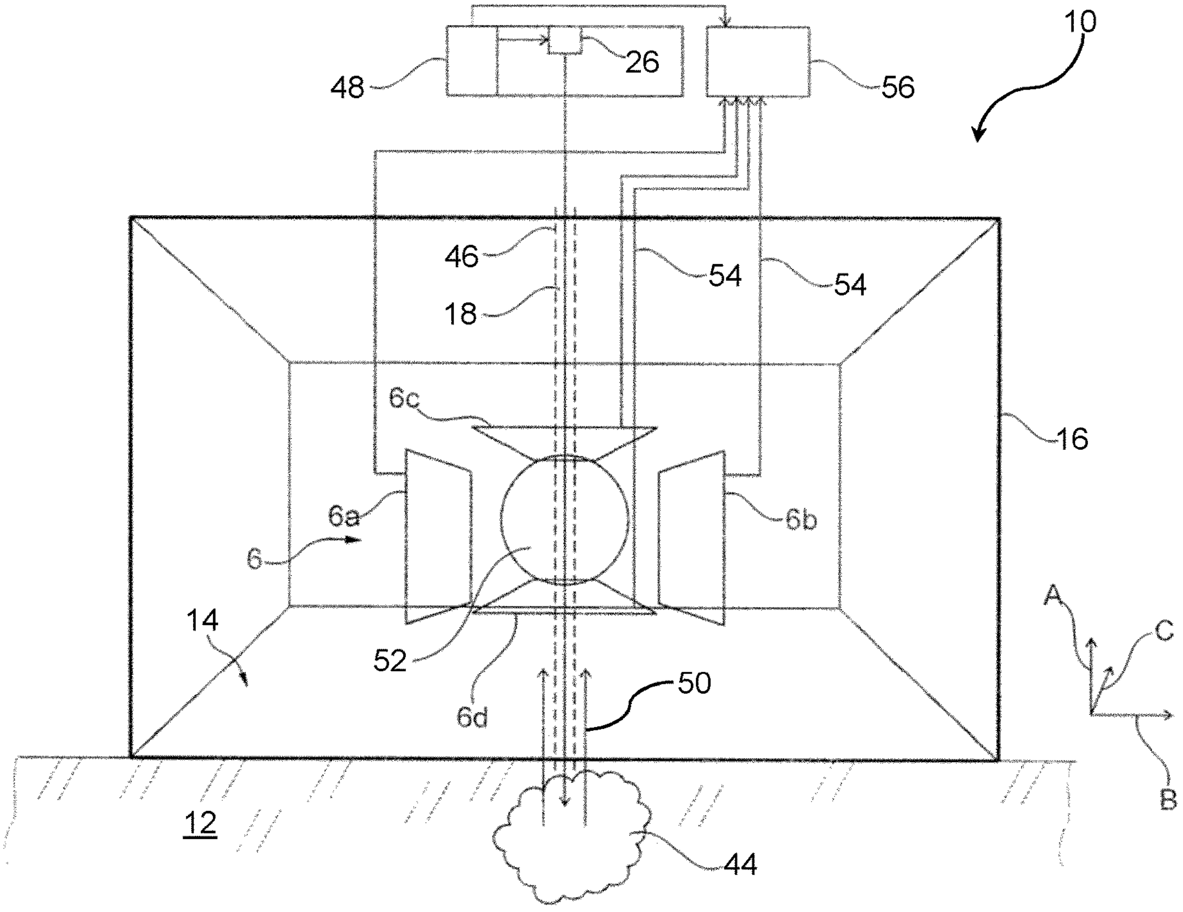
FIG. 5 is a schematic view of an apparatus suitable for carrying out embodiments of the invention relying on response signals based on piezoelectric response to heat or pressure waves received by the material subjected to the analysis.

FIG. 5 schematically shows an apparatus 10 which relies on the same general principle involving absorption heat pulses received by the measurement body 16 from the material 12 as that of FIGS. 1 and 3, but differs in the physical response exploited and the way the corresponding response signals are generated. Such an apparatus 10, as well as a large number of variations thereof are described in detail in WO 2019/11059782 incorporated herein by reference, such that a detailed description may be omitted herein. As before, the apparatus comprises a measurement body 16 having a surface 14 which is brought in contact or coupling with the skin of a finger 12. Also, a source 26 for an excitation light beam 18 with modulated intensity is provided, which is irradiated into a region 44 underneath the surface of the skin 12 and absorbed therein. In this embodiment, the excitation light beam 18 runs through a bore 46 indicated by hashed lines through the measurement body 16, such that the measurement body 16 itself need not be transparent for it.

A control unit 48 is provided for modulating the intensity of the excitation light beam 18. This can generally be done in various ways, including a mechanical chopper or an element having a transmissivity or reflectivity that can be electronically controlled. However, in preferred embodiments, the intensity is modulated by modulating the on/off times of the excitation light source 26 as well as the operating current during the on-times thereof.

A thermal wave caused by the time varying absorption of the intensity modulated excitation beam 18 in the region 44 of the skin 12, which is symbolically represented by arrows 50, enters the measuring body 16 where it can be detected in a detection region 52 which has piezoelectric properties. Pressure changes associated with received heat 50 or pressure waves lead to electrical signals that can be recorded with electrodes 6*a* to 6*d*, which are connected via conducting leads 54 with an evaluation device 56 for analyzing the material (the skin of FIG. 12), which may be a digital processing device, for example a microcontroller or processor or a computer. In this case, the change in pressure resembles the physical response of the measurement body 16, or other component included therein, to heat received from the material 12 upon absorption of the excitation radiation, which is detected using the piezoelectric properties of the measurement body 16 and the electrodes 6*a* to 6*d*, and which leads to electrical signals representing the response signal that is indicative of the degree of absorption of excitation radiation 18.

Figure 6:
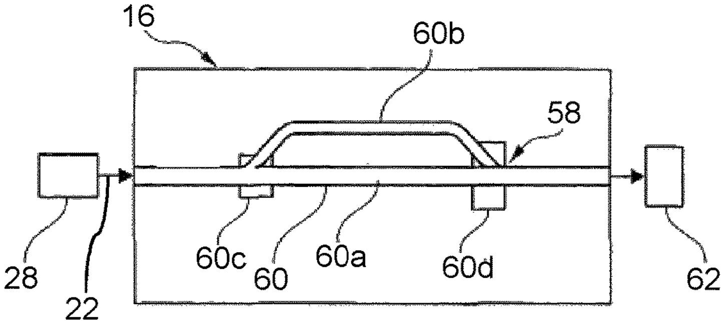
FIG. 6 is a schematic view of an apparatus suitable for carrying out embodiments of the invention relying on response signals based on interferometrically detected phase changes in a detection light beam.

In alternative variants suggested by the present applicant, as for example disclosed in international application PCT/EP2019/064356 included herein by reference, the detection device may comprise an interferometric device allowing for assessing said change in phase of a first part of the detection beam with respect to a second part of the detection beam, wherein only one of the parts of the detection beam passing through a measurement arm is affected by the effects of the heat or pressure wave in the measurement body, and generates a response signal indicative of said change in phase. In this case, the physical response of the measurement body 16 (or a component included therein) to heat received from said material 12 upon absorption of said excitation radiation 18 is again a local change in index of refraction, while the response signal is in this case an interferometric signal reflecting a change in the phase of the detection beam due to the local change in refractive index. This is schematically illustrated in FIG. 6, where a measurement body 16 is shown which is to be brought in contact with the material (such as the finger, not shown in FIG. 6). In this case, the measurement body 16 may be a silicon substrate in which a light guiding structure 58 is provided, which forms an interferometric device 60. The interferometric device 60 forms a Mach-Zehnder interferometer, having a measurement arm 60*a* and a reference arm 60*b*. Detection light 22 generated by a detection light source 28 is fed into the light guiding structure 58 and is splitted by a splitter 60*c* into a portion or a part of the detection beam travelling along the measurement arm 60*a* and a portion or part travelling along the reference arm 60*b*, which portions are then united by a combiner 60*d*. The measurement body 16 is used or arranged such that the reference arm 60*a* is exposed to heat received from the skin upon absorption of excitation light, but not, or at least to a much lesser extent, the reference arm 60*b*. Due to received heat, the refractive index in the measurement arm 60*a* will change, which in turn leads to a phase shift of the detection light 22 travelling along the measurement arm 60*a*. Since the light travelling along the reference arm 60*b* is unaffected by the heat received, there will be a change in relative phase of the two portions of light combined by the combiner 60*d*, which leads to an interference pattern that can be detected using a detector 62.

Figure 7:
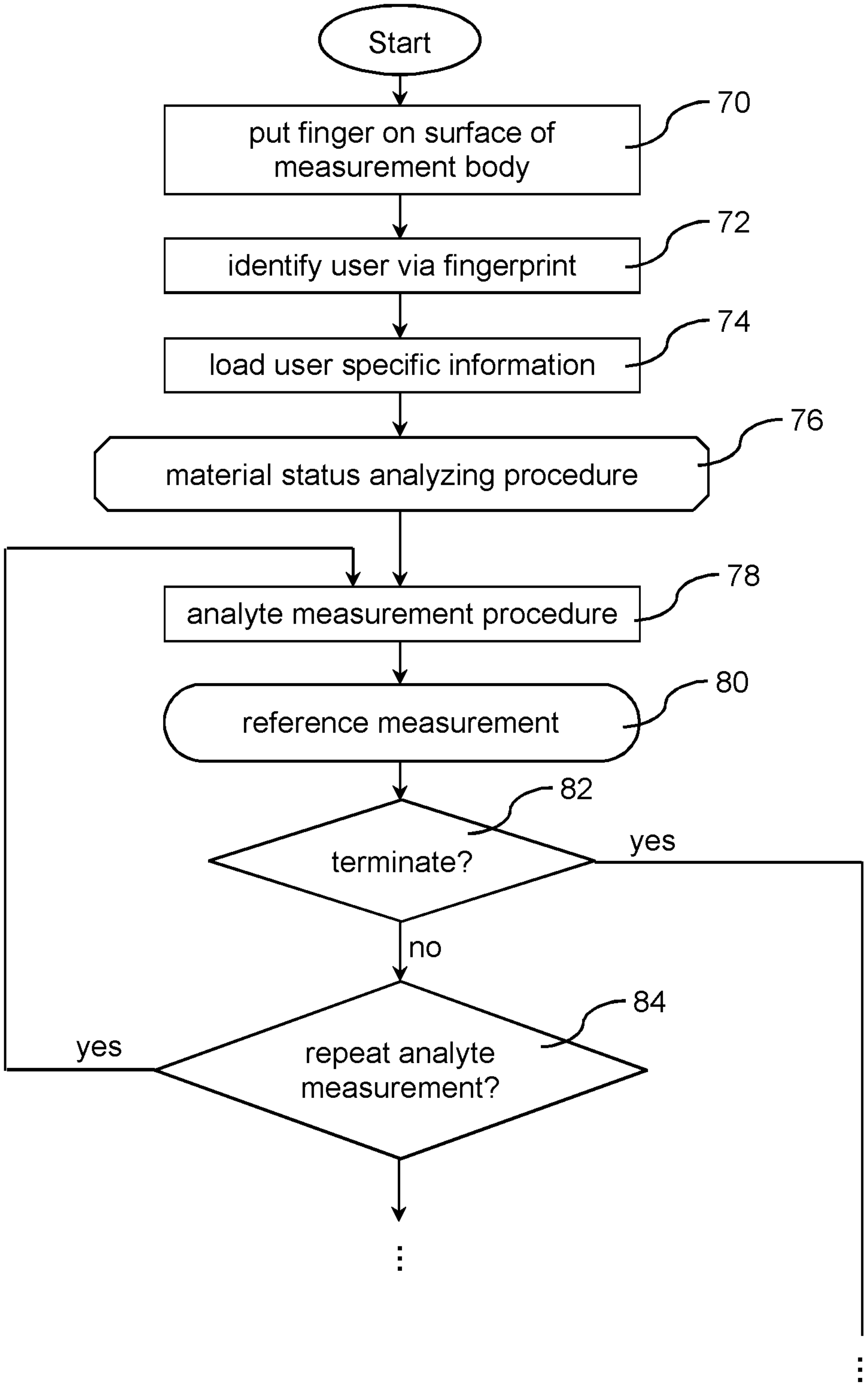
FIG. 7 is a flow diagram illustrating a method according to an embodiment of the invention, including an analyte measurement procedure, a material status analyzing procedure and a reference measurement.
Figure 7:
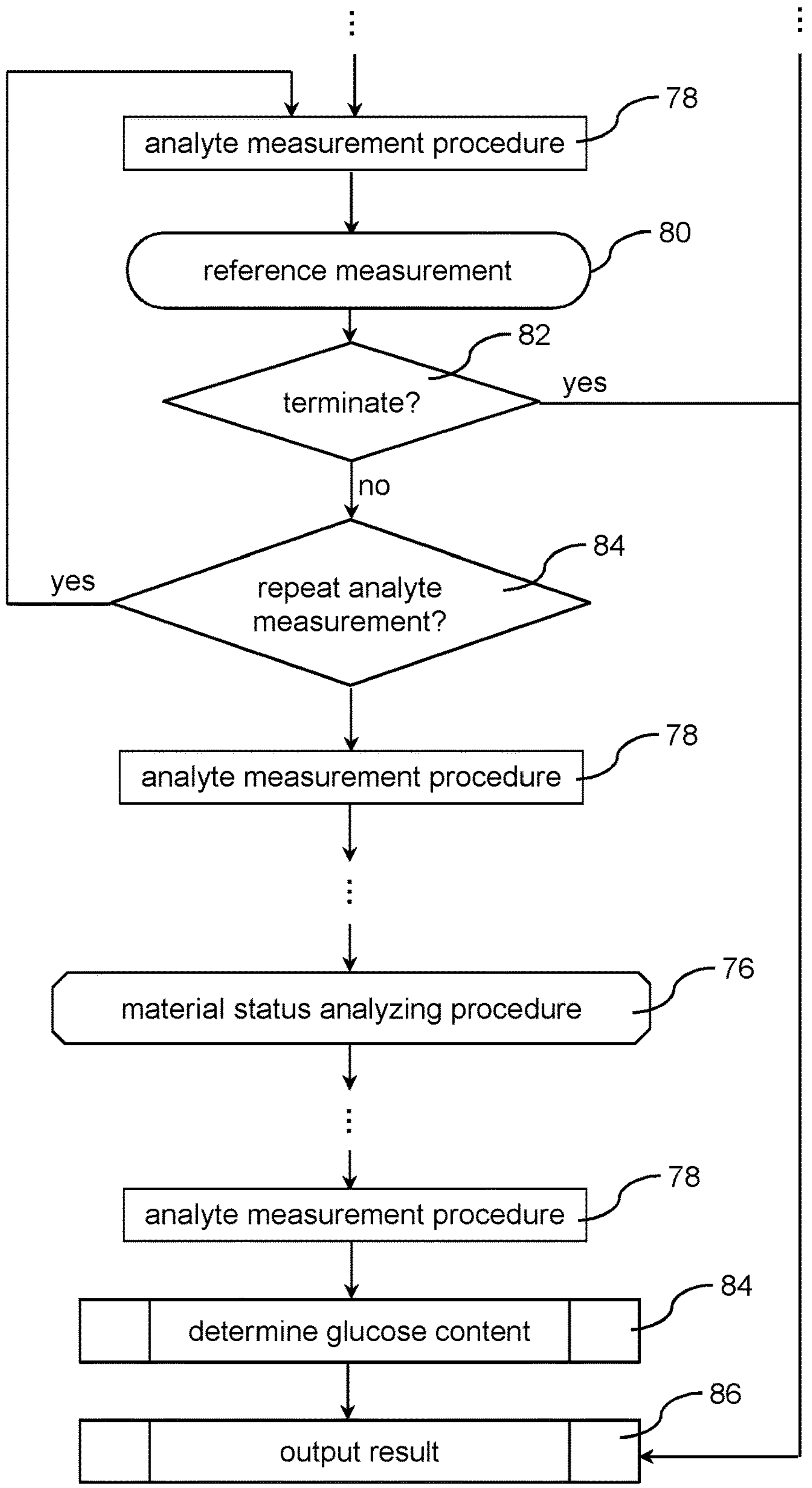

With reference to FIG. 7, a method of analyzing a material comprising at least one analyte according to an embodiment of the present invention is described. In this embodiment, the analyte is glucose and the material is the skin of the finger of a person.

The method starts at step 70 in which the user puts his or her finger 12 on a contact surface 14 of a measurement body 16 of the type shown in any of FIG. 1, FIG. 3, FIG. 5 or FIG. 6.

In step 72, the user is identified via his or her fingerprint. For this purpose, a camera as shown under reference sign 32 in FIG. 3 or other imaging device can be used. Once the user is identified, user-specific information is loaded into a control unit that eventually carries out the analysis. This control unit could for example be formed by the internal control unit 34 shown in FIG. 3, which is part of a portable device 10, or an external data processing device as shown under reference sign 36 in FIG. 3. The user-specific information may include specific data that enable a precise measurement of the glucose and may include for example calibration parameters previously established for the user.

In addition to this user-specific information, in subsequent step 76 a material status analyzing procedure is carried out. As was explained in the summary of the invention above, the material status analyzing procedure allows for determining the present status of the "material", i.e. in this case of the skin.

Figure 8:
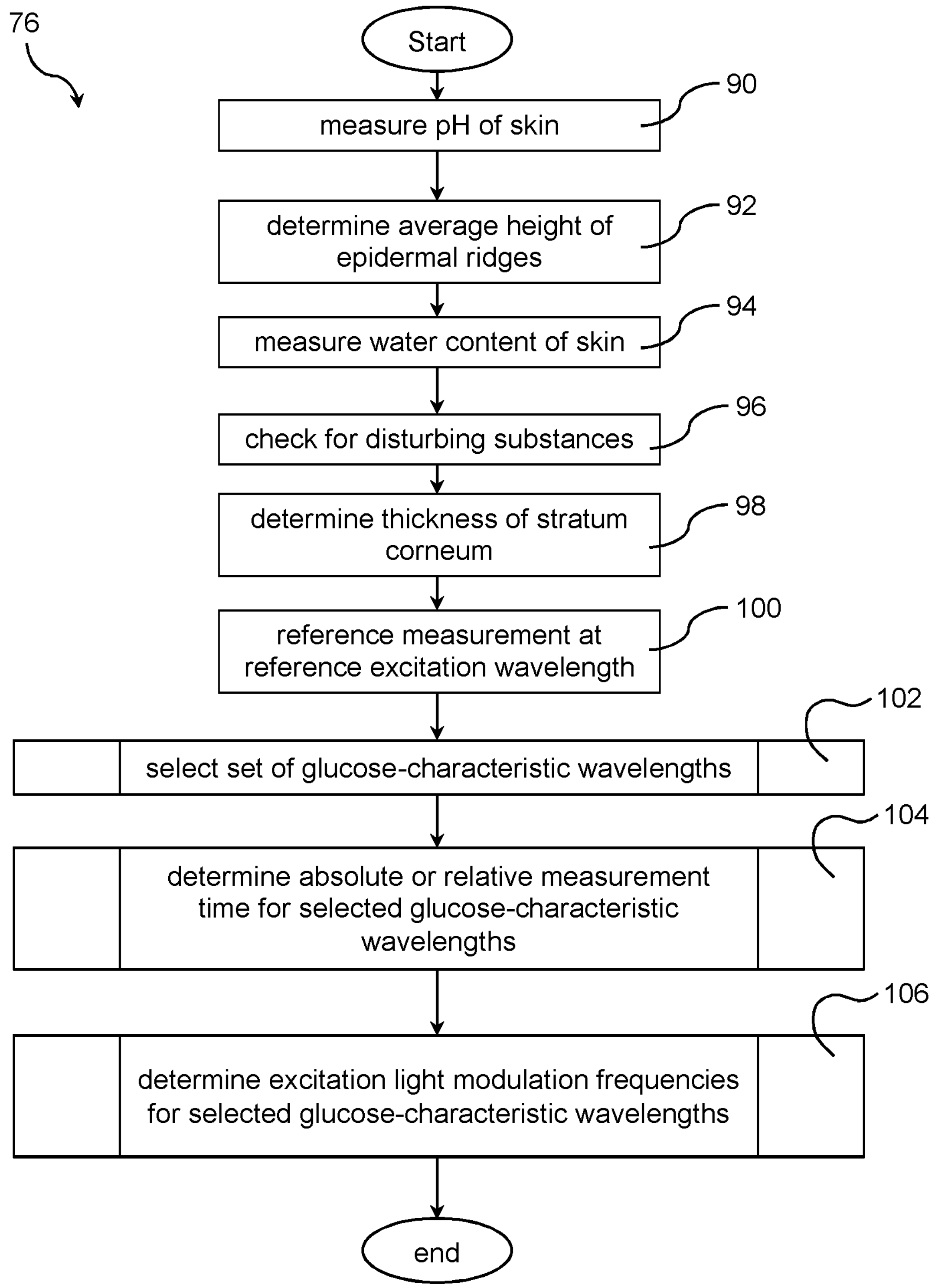
FIG. 8 is a flow diagram illustrating detailed steps associated with the material status analyzing procedure of FIG. 7.

The steps of the material status analyzing procedure 76 are explained in more detail with reference to FIG. 8. As part of the material status analyzing procedure, in step 90, the pH value of the skin is measured, using for example a pH-sensor 42 shown in FIG. 3.

In the following step 92, the average height of the epidermal ridges of the finger 12 of the user is determined using a dedicated sensor which is also integrated with the apparatus (not shown). The "average height of the epidermal ridges" corresponds to the average height in the current situation, i.e. when the finger 12 rests on the contact surface 14 of the measurement body 16. As such, this average height depends on both, the natural structure of the epidermis, but also on the current contact pressure applied. In particular, the average height of the epidermal ridges may apply to the region where the excitation light beam 18 enters the skin, since this is the region where good optical coupling is needed.

In the next step 94, the water content of the skin is measured. Again, in the embodiment shown, this is done using a dedicated corneometric sensor shown under reference sign 40 in FIG. 3. The corneometric sensor 40 is arranged in the apparatus 10 of FIG. 3 such that it is in contact with the finger 12 when the latter rests on the contact surface 14 of the measurement body 16. The corneometric sensor 40 in the present embodiment measures the water content in the upper layer of the skin based on an AC impedance when an AC voltage is applied to corresponding electrodes, in particular interdigital electrodes.

In subsequent step 96, it is checked for "disturbing substances" in the skin. As understood herein, "disturbing substances" are substances that are different from the one or more analyte, i.e. in this case different from glucose, but exhibit significant absorptivity of excitation radiation at at least one among a set of predetermined analyte-characteristic-wavelengths that are to be used for measuring the analyte. An important example of such a disturbing substance in case of glucose measurement is lactate, which can be found in varying concentrations in the skin, and which has absorption bands that partially overlap with absorption bands of the glucose molecule. In order to properly determine the concentration of the glucose, it is important to determine if, and if yes, to which extent a current concentration of lactate in the skin could influence the glucose measurement.

It is emphasized that the lactate concentration is a parameter that changes not only from person to person, but for each individual from day-to-day or even by the hour. Accordingly, the lactate concentration is nothing that could be accounted for with any pre-stored user specific information that is retrieved in step 74.

Figure 9:
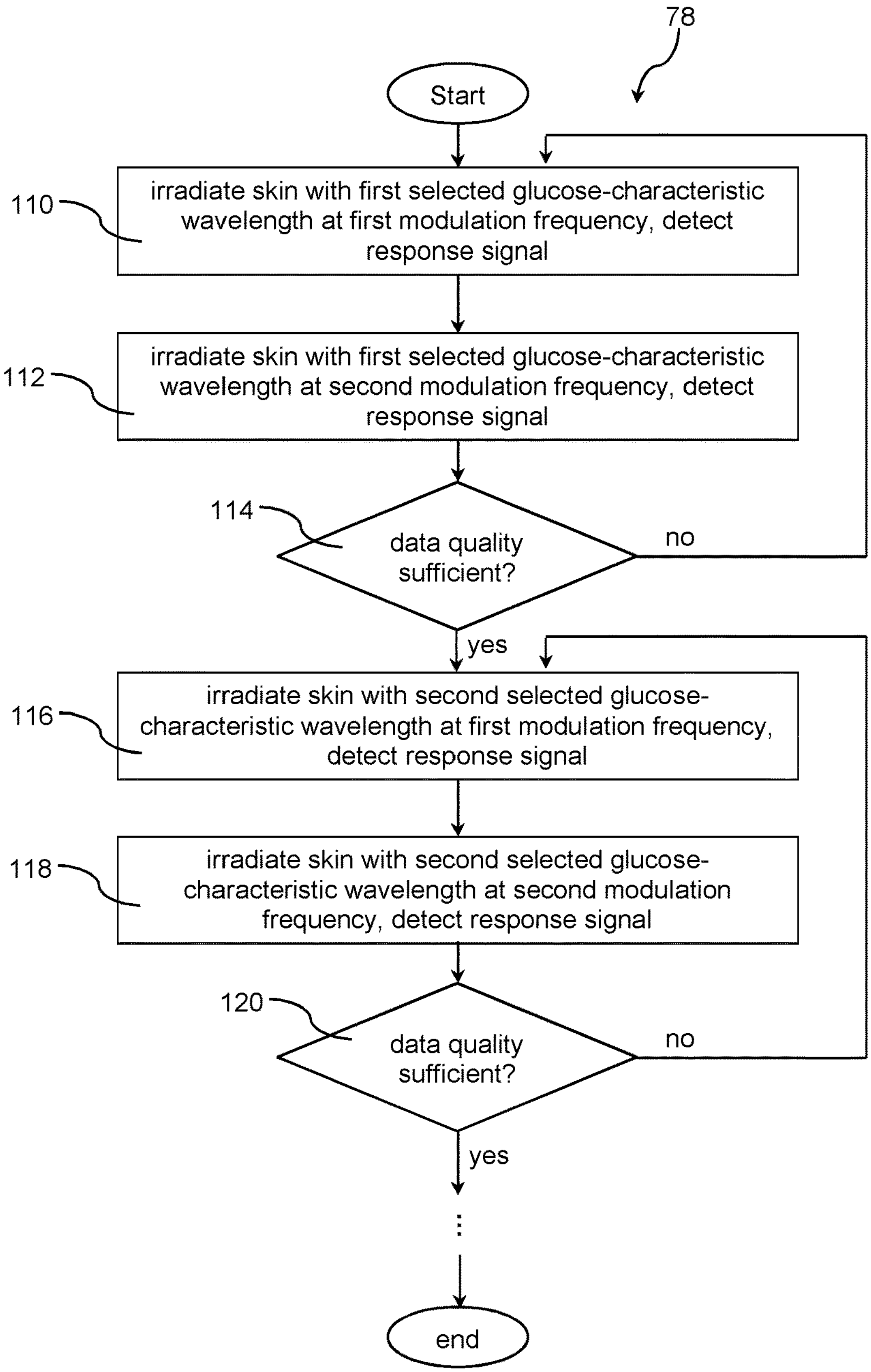
FIG. 9 is a flow diagram illustrating detailed steps associated with the analyte measurement procedure of FIG. 7.

In the following step 98, the thickness of the stratum corneum is determined. The stratum corneum is the uppermost layer of the skin and does not contain the interstitial fluid comprising the glucose that is to be measured. However, it cannot be avoided that a significant part of the excitation light is absorbed in the stratum corneum, nor can it be avoided that a considerable contribution of each response signal will reflect absorption within the stratum corneum. Instead, the response signal will always account for absorption of excitation light in a depth range from the surface of the skin up to a depth that is defined by the thermal diffusion length as explained above, and hence generally include the stratum corneum. However, knowing the thickness of the stratum corneum is important, because this will allow for both, properly choosing the maximum depth range of the absorption measurement extending sufficiently far beyond the stratum corneum, as well as a suitable depth range for measuring absorption in the stratum corneum only, which can then be used to generate a compensated signal mainly reflecting the absorption in the interstitial fluid, as will be explained in more detail with reference to FIG. 9.

The thickness of the stratum corneum can be assessed directly or indirectly based on response signals established for identical wavelengths of the excitation radiation but for different intensity modulation frequencies of said excitation radiation, wherein the excitation wavelength is chosen such as to match an absorption band of a substance present with different concentrations in the stratum corneum and in the interstitial fluid. Indeed, since the glucose itself is found at higher concentration in the interstitial fluid and at lower concentration in the stratum corneum, the thickness of the stratum corneum can be assessed when conducting a series of measurements with an excitation wavelength corresponding to an absorption peak of the glucose and with varying modulation frequencies, and hence varying depth ranges. At a depth range where the interstitial fluid is reached, this will become noticeable by an increased absorption by the glucose molecules that are included therein.

Based on information gained in steps 90 to 100, in step 102, a set of glucose-characteristic-wavelengths to be used in the analyte measurement procedure can be selected as a subset of the complete set of all available glucose-characteristic wavelengths. That is to say, the apparatus 10 according to the described embodiment provides for a predefined set of glucose-characteristic-wavelengths that may in principle be used, but in an actual analyte measuring procedure, only a most suitable subset thereof will be applied. For example, the excitation light source 26 shown in FIG. 3 may be an array of quantum cascade lasers, each having a dedicated excitation wavelength, such that the predefined set of excitation light wavelengths corresponds to the set of wavelengths of the quantum cascade lasers in the array. In other embodiments, the excitation light source 26 may be a wavelength-tunable quantum cascade laser, which in principle is capable of providing a continuum of wavelengths, but in this case too, there will typically be a predefined set of predetermined analyte-characteristic-wavelengths to be used in the analyte measurement procedure, and from this, in step 102, a suitable subset is selected.

Figure 11:
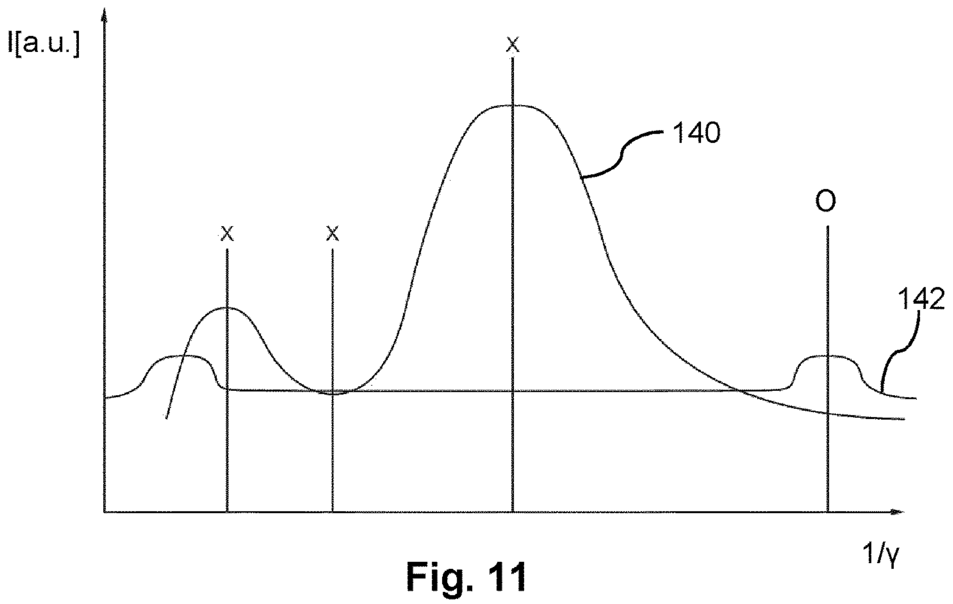
FIG. 11 is a schematic illustration of absorption spectra of an analyte and a disturbing substance with low concentration, as well as correspondingly selected excitation radiation wavelengths.

For example, depending on whether step 96 revealed a high concentration of a disturbing substance or not, a selection among the predefined glucose-characteristic-wavelengths can be made, as will be explained with reference to FIGS. 11 and 12. FIG. 11 shows two schematic absorption spectra, namely an absorption spectrum 140 of the analyte as well as an absorption spectrum 142 of a disturbing substance. FIG. 12 shows the same spectra, except that in this case, the concentration of the disturbing substance is higher, such that its absorption spectrum 142 is enlarged. In order to estimate the concentration of the disturbing substance, in step 96, an absorption measurement is carried out at a wavelength corresponding to the right peak in the absorption spectrum 142 of the disturbing substance, where the wavelength position is indicated with the circle symbol "O". This is a suitable wavelength for assessing the concentration of the disturbing substance, because this peak of the disturbing substance spectrum does not overlap with any significant absorption of the analyte. As seen in FIGS. 11 and 12, the disturbing substance has a further peak on the left, which is however at least partially overlapping with the left peak of the analyte spectrum 140. If the measurement at the right peak of the disturbing substance spectrum 142 carried out in step 96 reveals that the concentration is comparatively low, as is the case in the illustration of FIG. 11, it will not significantly interfere with the absorption measurement at the left peak of the analyte spectrum 140, and accordingly this left analyte spectrum peak would be a suitable analyte-characteristic-wavelength to be used in the analyte measurement procedure. Accordingly, three suitable exemplary wavelengths to be used in the analyte measurement procedure are indicated in FIG. 11 by the x-symbols, namely wavelengths corresponding to the two peaks as well as the wavelength corresponding to a local minimum in between.

However, if the measurement of step 96 reveals that the concentration of the disturbing substance is high, as schematically shown in FIG. 12, the analyte-characteristic-wavelength corresponding to the left peak of the analyte spectrum 140 would no longer be a good choice, since it is overlapped with significant absorption by the disturbing substance. Instead, as indicated in FIG. 12, in this case it may be preferable to use two analyte-specific-wavelengths close to the right (main) peak of the analyte spectrum, and devote a further one, as before, to the local minimum, thereby allowing for obtaining a more precise measurement of the right absorption peak of the analyte. This type of selection is made in step 102.

Figure 14:
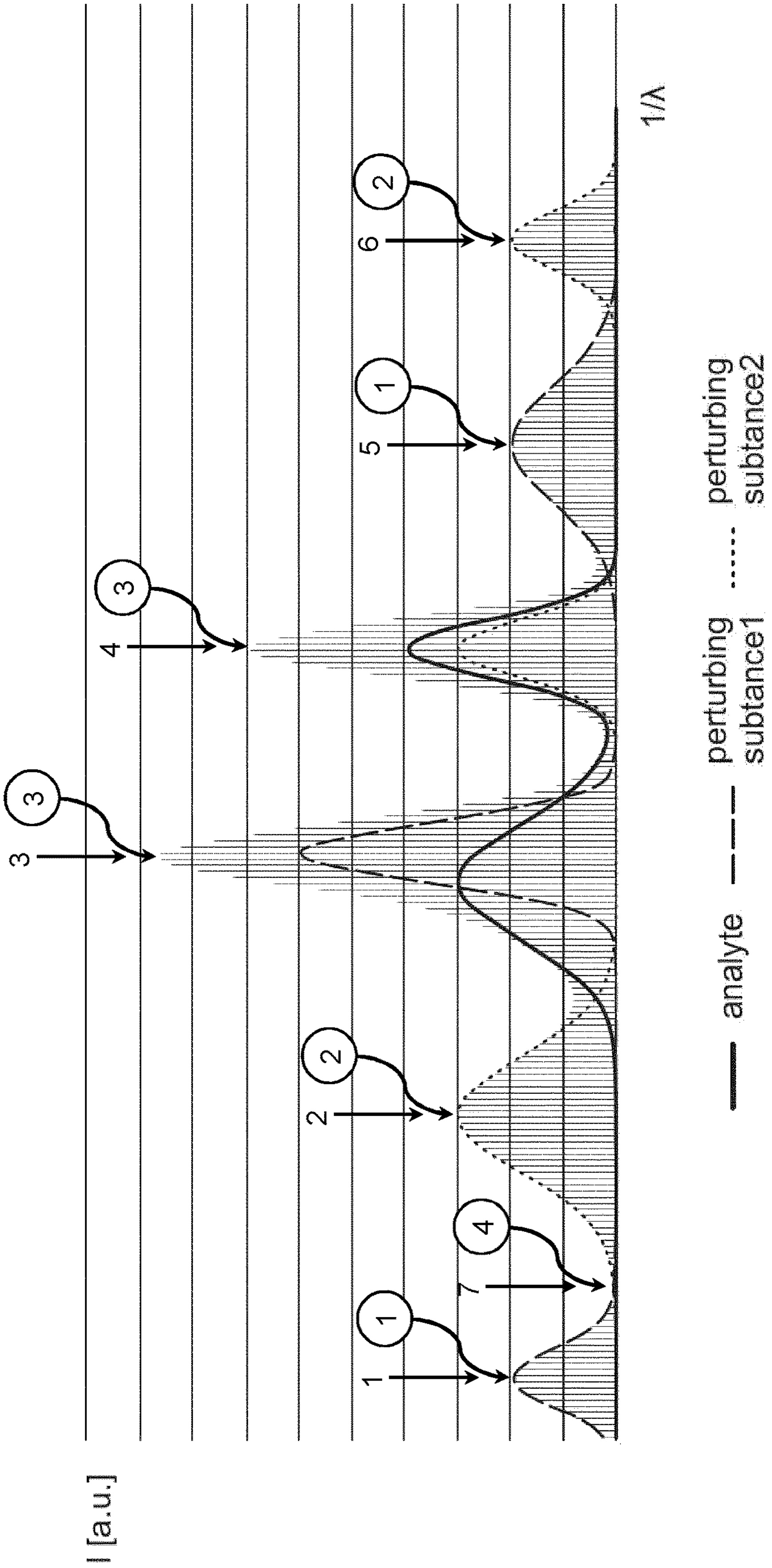
FIG. 14 is a schematic illustration of the absorption spectra of an analyte and to perturbing substances, as well as of the combined absorption spectrum.

FIG. 14 shows a more complicated situation, where the material includes one analyte (solid line) and two perturbing substances represented by the long dashed and short dashed lines in the absorption spectrum illustrated in FIG. 14. The total absorption spectrum is represented by the vertical lines. It is seen that the analyte absorption spectrum has two peaks, of which, however, the left one overlaps with perturbing substance 1 and the right one overlaps with perturbing substance 2.

In order to determine the concentration of the analyte, the straightforward procedure would be to measure all six peaks of the total spectrum, which are indicated by the vertical arrows with the corresponding numbers 1 to 6 representing measurement steps, as well as the background, which is subtracted in the spectrum shown in FIG. 14, but in the actual measurement is of course present, and which is determined by a seventh measurement at a wavelength indicated by the corresponding arrow. Then, knowing the general shape of the three spectra, from the seven measurements, the relative heights can be calculated and hence the concentration of the analyte can be determined. However, according to a preferred embodiment of the invention, measurements with different excitation wavelengths would be carried out simultaneously, meaning that only four measurements would have to be carried out. These four measurements are indicated in FIG. 14 by numbers 1 to 4 placed in circles.

Namely, in the first measurement, an absorption measurement would be carried out while simultaneously irradiating two absorption frequencies of the first perturbing substance, corresponding to the measurements 1 and 5 in the straightforward procedure. Then, in a second measurement, two isolated excitation peaks of the second disturbing substance would be measured, corresponding to the measurements 2 and 6 in the standard procedure, in a single step by simultaneously irradiating the material with the two corresponding excitation light frequencies. Since these measurements relate to the disturbing substances, they would be carried out in step 96 of the flow diagram of FIG. 8. Then, during the analyte measurement procedure, as a third measurement, an absorption measurement could be carried out in which the wavelengths corresponding to measurements 3 and 4 in the ordinary procedure are simultaneously irradiated. These wavelengths used in the third measurement are analyte-specific-wavelengths, namely wavelengths corresponding to or being at least close to an absorption maximum of the analyte. In addition, the background would be measured as a fourth measurement.

Accordingly, it is seen that step 102 of selecting a set of glucose-characteristic-wavelengths could also include selecting certain glucose-characteristic-wavelengths that are to be irradiated simultaneously, such as to obtain a response signal that is indicative of the simultaneous absorption of both analyte-characteristic-wavelengths, such as the wavelengths corresponding to the third measurement described above (third and fourth measurement according to the standard procedure). Potentially, the two excitation radiation beams with the two different wavelengths irradiated simultaneously may be modulated with different modulation frequencies in order to be in a position to separate the respective measurement signals. Knowing the general shape of the individual spectra of the analyte and the two disturbing substances, the relative heights, and eventually the concentration of the analyte can be determined also from the signals representing the sum of two absorption peaks. When using two or more excitation wavelengths simultaneously, more information can be obtained per measuring time, thereby increasing the efficiency of the analyte measurement procedure. Moreover, the result of measurements 1 and 2 carried out during the "check for disturbing substances" of step 96 of the material status analyzing procedure could be such that it is decided in step 102 that the overlap with these two disturbing substances is too large and that the analyte-characteristic-wavelengths associated with the two absorption peaks of the analyte spectrum (third and fourth measurement according to the standard procedure shown in FIG. 14) are not selected, and that other analyte-characteristic-wavelengths (not shown in FIG. 14) are selected instead.

Figure 13:
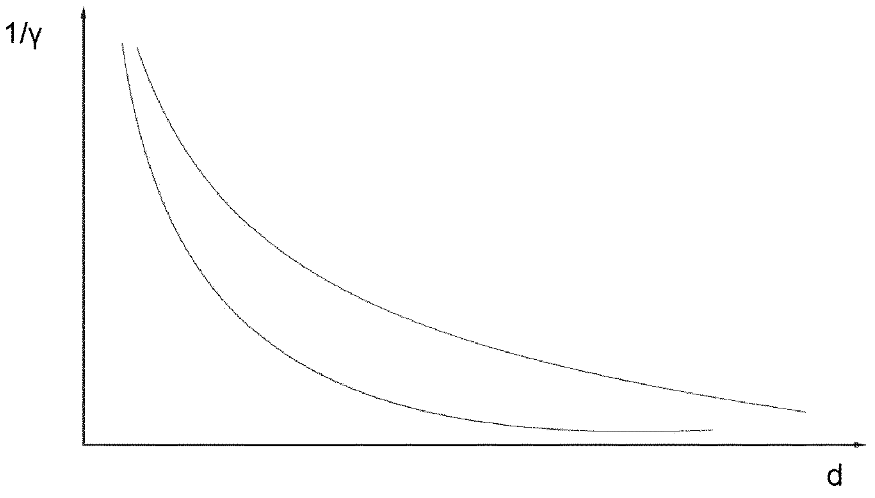
FIG. 13 illustrates the exponential decay of the intensity of excitation radiation with penetration depth due to water absorption for two different wavelengths.

A further example of how the set of glucose-characteristic-wavelengths can be selected in step 102 based on information gained in the measurements of steps 90 to 100 is explained with reference to FIG. 13. FIG. 13 shows the typical exponential decay of excitation light with increasing depth when penetrating into the skin. The intensity I(d) as a function of penetration depth d is hence given as $I(d)=I(d=0)\cdot\exp(-\alpha(\lambda)\cdot d)$, where $\alpha(\lambda)$ is a wavelength-dependent absorption coefficient. In practice, a substantial part of the absorption is due to water in the skin. It is found that in the wavelength region including the most useful absorption peaks of glucose for the purposes of the invention, i.e. a region between roughly 8 μm and 11 μm, the absorption coefficient $\alpha(\lambda)$ of water is lower for shorter wavelengths than for longer wavelengths. Although not shown to scale but exaggerated for illustration purposes, the upper curve in FIG. 13 would therefore correspond to a shorter wavelength among the possible analyte-characteristic-wavelengths, while the lower curve in FIG. 13 would correspond to a longer one. Accordingly, if in step 94 a high water content in the skin is found, this would indicate that the absorption of water is severe, and that it is difficult to obtain sufficient intensity of excitation light in deeper regions of the skin where the interstitial fluid resides. As was explained above, the problem with large absorption coefficients $\alpha(\lambda)$ is not only that the intensity of the excitation light in the depth range of interest is low and hence the contribution of the absorption in this depth range to the response signals is small, which would seem to be a problem that could in principle be overcome by longer measurement times and suitable data processing. Instead, for reasons given above, there is a fundamental problem when the optical absorption length $\mu_t(\lambda)$, which is the inverse of the a wavelength-dependent absorption coefficient $\alpha(\lambda)$, drops below the thermal diffusion length $\mu_t$ (f). Accordingly, for high water content determined in step 94, preference is given to shorter glucose-characteristic-wavelengths in the selection of step 102 to benefit from the lower absorption coefficient $\alpha(\lambda)$ and hence longer optical absorption length $\mu_\alpha(\lambda)$.

In a further step 104 of the material status analyzing procedure 76, an absolute or relative measurement time for selected glucose-characteristic-wavelengths is determined. In other words, instead of merely selecting which of the predefined glucose-characteristic-wavelengths are to be used and which ones are to be left out in the analyte measurement procedure, as is the case in step 102, in step 104 relative measurement times or absolute measurement times can be assigned to the selected glucose-characteristic-wavelengths, such that the precious measurement time is devoted to selected wavelengths in a manner that—based on the results of steps 90 to 100—the measurement accuracy is expected to be maximized.

Finally, in step 106, the excitation light modulation frequencies for selected glucose-characteristic-wavelengths are determined. As was explained above, the frequency of the intensity modulation of the excitation light determines the thermal diffusion length $\mu_t(f)$ and hence the depth range covered by the measurement. If the determination of the stratum corneum thickness in step 98 for example indicates a large stratum corneum thickness, this would call for lower modulation frequencies to allow for longer thermal diffusion lengths. In step 106, the selection of the modulation frequencies is carried out in such a way that with all other characteristics of the material status the same, a lower main frequency of the modulation is chosen for higher stratum corneum thicknesses.

For example, as explained above, step 104 could rely on a predetermined threshold value of the stratum corneum thickness (or another parameter representing the same), and the modulation frequency could be adjusted based on whether the stratum corneum thickness is below the threshold (in which case a higher modulation frequency would be chosen) or above the threshold (in which case a lower modulation frequency would be chosen). In alternative embodiments, there could be several stratum corneum thickness ranges and associated modulation frequencies, where the modulation frequencies for larger stratum corneum thicknesses are lower than for smaller stratum corneum thicknesses, or the modulation frequency could be determined based on a continuous function defining modulation frequencies as a function of the determined stratum corneum thicknesses. Any way of determining the modulation frequency as a function of determined stratum corneum thickness may be employed, as long as it is ensured that with all other characteristics of the material status the same, a lower main frequency of the modulation is chosen for higher stratum corneum thicknesses.

Note that in step 106 generally at least two excitation light modulation frequencies are determined for some or each selected glucose-characteristic-wavelength, namely a first (lower) modulation frequency intended to cover significant portions including interstitial fluid, as well as a second (higher) modulation frequency, which is intended to measure response signals for compensating the absorption in higher layers of the skin where no or little interstitial fluid is present, in particular the stratum corneum. In some embodiments, at least the second modulation frequency is determined in step 106 according to the determined thickness of the stratum corneum.

Moreover, in some embodiments, the selection or determination of the excitation light modulation frequencies in step 106 also depends on the water content determined in step 94. If a high water content is determined, and hence a short optical absorption length $\mu_\alpha(\lambda)$ must be expected, this would be a reason to choose not too low excitation light modulation frequencies, to ensure that the thermal diffusion length $\mu_t(f)$ is equal to or shorter than the optical absorption length $\mu_\alpha(\lambda)$.

With reference again to FIG. 7, after completion of the material status analyzing procedure 76, an analyte measurement procedure 78 is carried out. The analyte measurement procedure is explained with reference to the flow diagram of FIG. 9. In step 110 of FIG. 9, the skin is irradiated with a first selected glucose-characteristic wavelength at a first modulation frequency, and the corresponding response signal is detected. In the following step 112, the skin is irradiated with the same first selected glucose-characteristic wavelength, but at a second modulation frequency, which is higher than the first modulation frequency, and the corresponding response signal is detected. The first modulation frequency is selected sufficiently low such that the response signal reflects at least in part absorption of excitation light within the interstitial fluid. In some embodiments, the first modulation frequency f is chosen in a range of $4 \cdot f_{min} > f > f_{min}$, preferably $3 \cdot f_{min} > f > f_{min}$, and most preferably $2 \cdot f_{min} > f > f_{min}$. Herein, as derived above, $f_{min}$ is defined as $f_{min} = k_t \cdot \alpha(\lambda)^2 / (2 \cdot \rho \cdot C_p)$, and $k_t$, $\rho$, and $C_p$ are again the thermal conductivity, the density and the specific heat capacity of the tissue, respectively, and $\alpha(\lambda)$ is the absorption coefficient for the first selected glucose-characteristic-wavelength $\lambda$ in said tissue.

Simply speaking, the second modulation frequency is chosen to cover a shallower depth range of the skin that is not of interest, i.e. those ranges that do not contain appreciable amounts of interstitial fluid and their glucose concentration therefore does not reflect the current glucose concentration in the interstitial fluid, and it is mainly recorded to be subtracted from the response signal associated with the first modulation frequency, after suitable normalization, to arrive at a corrected signal that as closely as possible reflects the absorption of glucose in the interstitial fluid. A suitable normalization factor could for example be the ratio of response signals corresponding to measurements with the first and second modulation frequencies at a wavelength where the absorptivity of glucose is vanishing, as for example at 1180 cm-1 (see FIG. 2). With this normalization factor, and without any glucose absorption, the difference between the response signals at the first and second modulation frequencies would be zero. Then, using the same normalization factor for measurements with the first and second modulation frequencies at a glucose-characteristic-wavelength, the difference between the two measurements would be a measure of the glucose absorption in the deeper range of the skin that is accessible only by the first modulation frequency, but not by the second modulation frequency.

In step 114, it is checked whether the data acquired in steps 110 and 112 have sufficient quality. For this purpose, for example, a signal-to-noise ratio of the response signal or a quantity derived from it is determined. If it is found that the data quality is not sufficient yet, the procedure returns to step 110 to collect more data. This way, it is ensured that sufficient measurement time is devoted to said first selected glucose-characteristic-wavelength to obtain measurement results of sufficient quality.

If the data quality is found to be sufficient, the process proceeds to step 116, where the procedure of steps 110 to 114 are repeated in steps 116 to 124 for the second selected glucose-characteristic wavelength. This procedure is continued for some or all selected glucose-characteristic wavelengths and the corresponding first and second modulation frequencies. Indeed, as is seen in FIG. 7, several instances of the analyte measurement procedure 78 are provided, interspersed with reference measurements 80 and possibly further material status analyzing procedures 76, so that it is not necessary that all selected glucose-characteristic-wavelengths are covered in each instance of the analyte measurement procedure 78.

Importantly, both the glucose-characteristic-wavelengths and the corresponding first and second modulation frequencies used in the analyte measurement procedure 78 are optimally selected to account for the material (skin) status as determined in the material status analyzing procedure 76 which was carried out immediately prior to the analyte measurement procedure, and without lifting off or even moving the finger 12 on the contact surface 14 of the measurement body 16.

Figure 10:
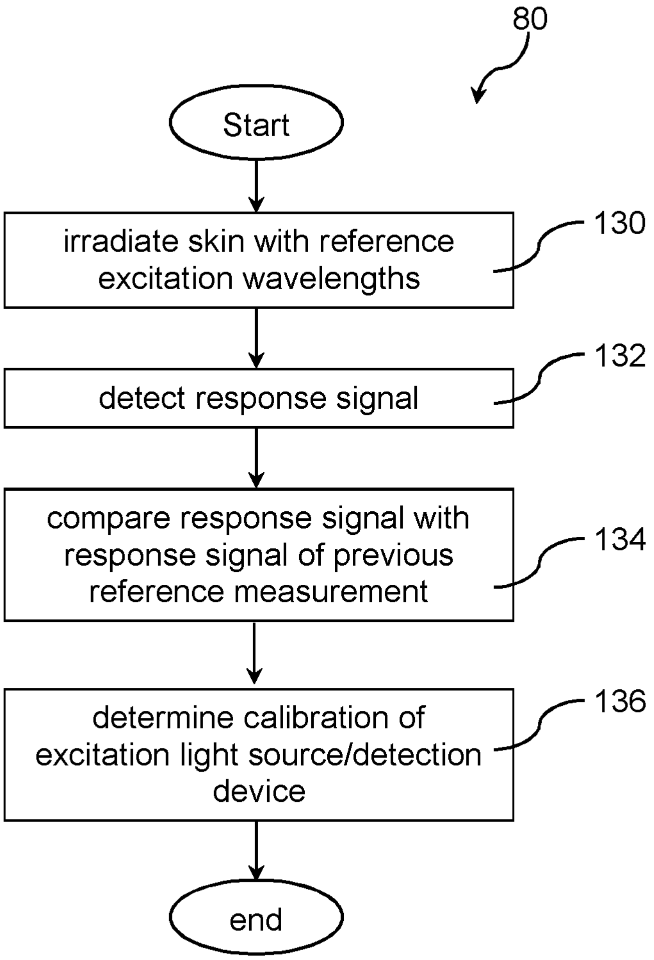
FIG. 10 is a flow diagram illustrating detailed steps associated with the reference measurement of FIG. 7.

With reference again to FIG. 7, in the next step 80 a reference measurement is carried out. The reference measurement 80 will be explained with reference to the flow diagram of FIG. 10. In step 130, the skin is irradiated with one or more reference excitation wavelengths, and in step 132, a corresponding response signal is detected. The reference wavelength is a wavelength that is different from any of the analyte-characteristic-wavelengths, and it is a wavelength for which the absorption of the glucose is low. In step 134, the response signal is compared with a response signal of a previous reference measurement. The previous reference measurement could for example be the reference measurement carried out as step 100 in the material status analyzing procedure 76. Moreover, several instances of the reference measurement 80 are interleaved with the analyte measurement procedures for different wavelengths, such that there will generally be earlier reference measurements 80 which can be used for comparison of the response signals.

Based on the comparison, calibrations of the excitation light source 26 or the detection device can be determined, to thereby account in real time for drifts in the light source, in the detection device or other variations, for example changes in the optical or thermal coupling between the finger 12 and the measurement body 16 that can be compensated for by recalibrating one or both of the excitation light source 26 and the detection device.

With reference again to FIG. 7, one result of the reference measurement could be that the analyte measurement procedure is flawed, for example because the positioning of the finger 12 on the measurement body 16 has changed such that thermal or optical coupling is insufficient. Accordingly, in step 82 it is decided whether the result of the reference measurement 80 is such that the procedure should be terminated, in which case the process jumps to step 86 and outputs the termination as a result. This could for example involve an indication to the user that the finger 12 should be placed on the measurement body 16 again, and the procedure restarted.

If the reference measurement 80 does not indicate that the measurement should be terminated, in step 84 it is checked whether the reference measurement 80 indicates that the analyte measurement procedure 78 should be repeated. If this is the case, the procedure returns back to step 78.

As is further seen in FIG. 7, various instances of the analyte measurement procedure 78 and reference measurement 80 are repeated. This means that effectively, the analyte-wavelength-specific measurements carried out in the analyte measurement procedure 78 are interspersed with reference measurements 80, such that the analyte measurement procedure is accompanied in real time by the reference measurements, thereby allowing to monitor the analyte-wavelength-specific measurements in real time and to recalibrate the apparatus 10 accordingly in real time as well.

As is further seen in FIG. 7, the analyte measurement procedure 78 can also be interspersed with one or more further instances of the material status analyzing procedure 76. Importantly, during all instances of the analyte measurement procedure 78, material status analyzing procedure 76 and reference measurement 80, the finger 12 stays in contact with the contact surface 14 of the measurement body 16.

In step 84, the glucose content is determined based on the response signal measured in the various instances of the analyte measurement procedure 78, and the result is outputted in step 86.

Figure 15:
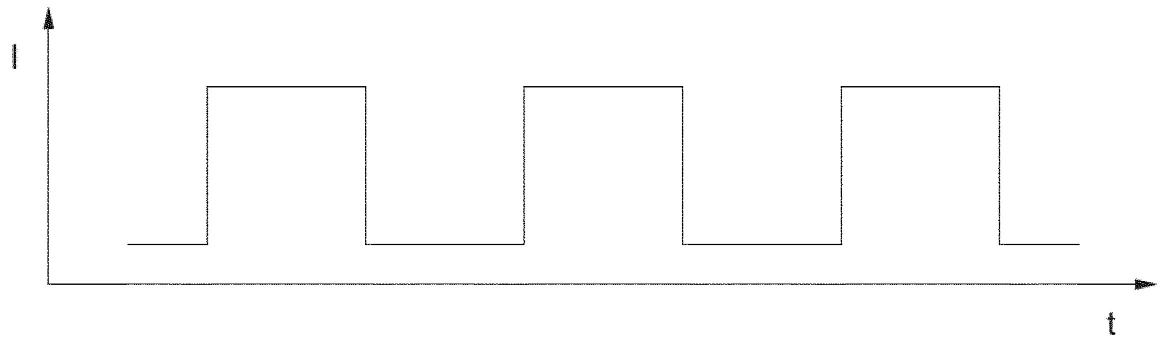
FIG. 15 is a schematic illustration of an excitation radiation modulation function, formed by a square wave with on-intervals and off-intervals of equal length.

FIG. 15 shows a typical modulation function for the intensity of the excitation light. The modulation function of the excitation radiation intensity is a square wave function alternating between zero ("off") and a maximum value ("on"), where the lengths of the on-intervals and the off-intervals are identical. The on-intervals can also be referred to as pulses, and suitable pulse lengths for the application described herein, i.e. glucose measurement in the skin, would be in a range of 2 to 50 ms.

Note that the modulation function can be obtained in various ways, for example using a chopper or a selectively transmissive element, or a corresponding control of the excitation light source 26. In preferred embodiments, the excitation light source 26 is formed by an array of quantum cascade lasers, and the modulation of the intensity in the relevant frequency range controlled by the electronic control thereof. In this case, the quantum cascade lasers are controlled to emit a pulse signal composed of "micro-pulses" having a frequency which is typically a factor of 10,000 to 100,000 times higher than the frequency of the modulation. These micro-pulses are hence on a much higher timescale as any of the thermal processes on which the measurement relies, and their fine structure can be completely ignored. Accordingly, in this case the intensity modulation would be the envelope of the plurality of micro-pulses.

Figure 16:
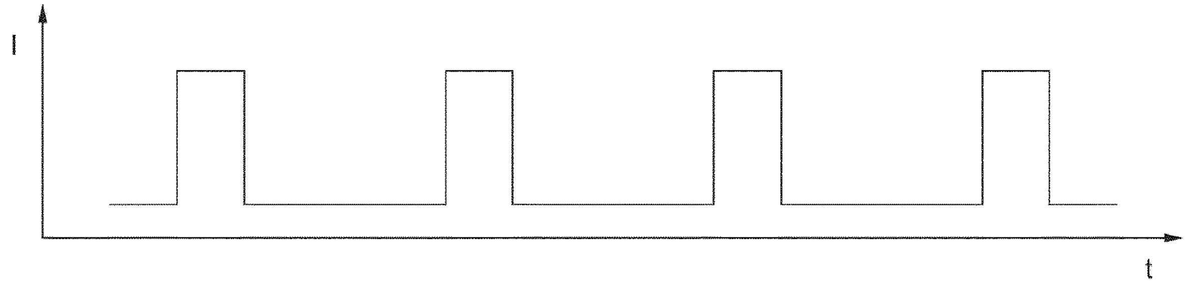
FIG. 16 is a schematic illustration of another excitation radiation modulation function, formed by a square wave with on-intervals that are shorter than the off-intervals.

The inventors have found that surprisingly, the accuracy and efficiency of the analyte measurement procedure can be improved if e.g. the relative length of off-intervals is longer than that of the on-intervals, without changing the frequency or period of the modulation signal, which period is the sum of the on- and off-interval, as is illustrated in FIG. 16.

It is seen that using the modulation of FIG. 16 instead of that of FIG. 15, better signal-to-noise ratios of the response signals can be obtained. As was explained above, according to the present understanding of the inventors, this is due to the fact that the response signals are "AC signals", in the sense that only the variation of the response signal with time can be assessed for estimating the degree of absorption. For this, it appears to be important that the physical response of the measurement body due to the heat received from the material can decay as much as possible before the next heat pulse is received. By increasing the off-times, there is more time for the physical response of the measurement body to decay, which leads to a better signal-to-noise ratio.

Note that the square wave modulation function would be the obvious choice at least for two reasons. The first reason is that for generating heat pulses, sharp excitation pulses with steep flanks would promise to give the best results, which is actually true in many applications. The second reason is that the square wave modulation is the easiest to establish in practice.

Nevertheless, the present inventors found that in spite of the apparent advantages of square wave modulations of the excitation light intensity, a sinusoidal modulation function may give better results in some applications, including the glucose measuring as described herein. This is a surprising finding, because the sinusoidal modulation function does not have the same sharp impulses found for square wave modulations which lead to particularly pronounced heat pulses in the skin that can be detected well using the apparatus of the invention. However, the inventors found that this disadvantage can be over-compensated in the specific situation at hand, where the analyte to be measured, i.e. the glucose, is mainly located in deeper layers of the material (the skin), which is only assessed by smaller modulation frequencies. When using a square wave signal, one has to distinguish between the main frequency thereof, which is the inverse of the repetition period of the signal, and the higher harmonic contributions to the signal, that are found in a Fourier series decomposition of the square wave signal. These higher frequency contributions again lead to response signals that correspond to absorption in shallower regions of the skin which are not of interest for the glucose measurement.

Accordingly, in preferred embodiments, the time modulation of said intensity of said excitation radiation is chosen such that the envelope of the intensity is approximately harmonic, i.e. is similar to a sinus function, such that in a Fourier decomposition of the intensity of the excitation radiation, of the total intensity associated with the dominant frequency and the $1^{st}$ to $9^{th}$ harmonics, at least 95% is associated with the dominant frequency and at least 97%, preferably at least 98% is associated with the dominant frequency and first harmonic.

Figure 17:
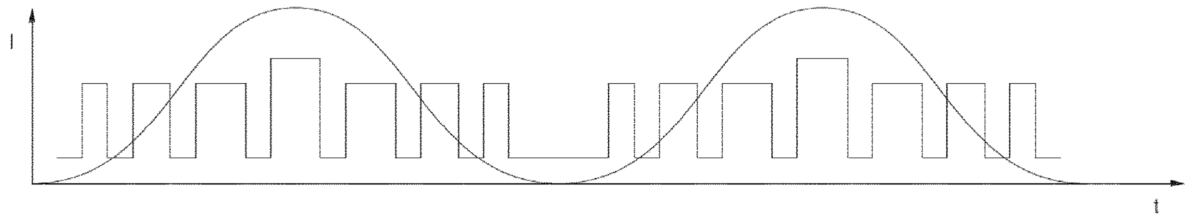
FIG. 17 is a schematic illustration of yet another excitation radiation modulation function, the envelope of which approximating a sinus function.

FIG. 17 is a schematic representation of the time-dependent intensity of excitation radiation having an envelope that matches a sinus function. The excitation light itself can again be constituted of pulses having different durations, different pulse densities or pulse amplitudes, as is generally known from PWM, PDM or PAM, and these techniques can be used to generate an envelope that is "approximately harmonic" in the manner defined above.

Note that FIG. 17 is only a schematic representation, and that in many applications, each period of the modulated intensity of the excitation radiation could be constituted by tenths of thousands of the "micro-pulses" referred to above, that could for example be provided by a quantum cascade laser, or quantum cascade laser element of a laser array. In preferred embodiments, these micro-pulses are modulated with respect to one or both of their length and their amplitude, wherein the amplitude can be modified in a certain range by modifying the operating current, to thereby lead to an envelope of the intensity that is at least "approximately harmonic". However, it is also possible to keep the micro-pulses constant with regard to one or both of their amplitude and frequency but to generate "macro-pulses", each macro pulse formed by a sequence of a plurality of micro-pulses, wherein the duration of each macro pulse is still considerably shorter than the period of the envelope of the excitation radiation intensity. Then, the desired envelope of the excitation radiation can be obtained by adjusting one or more of the length, frequency and amplitude of the macro-pulses accordingly in a manner generally known from PWM, PDM or PAM.

Figure 18:
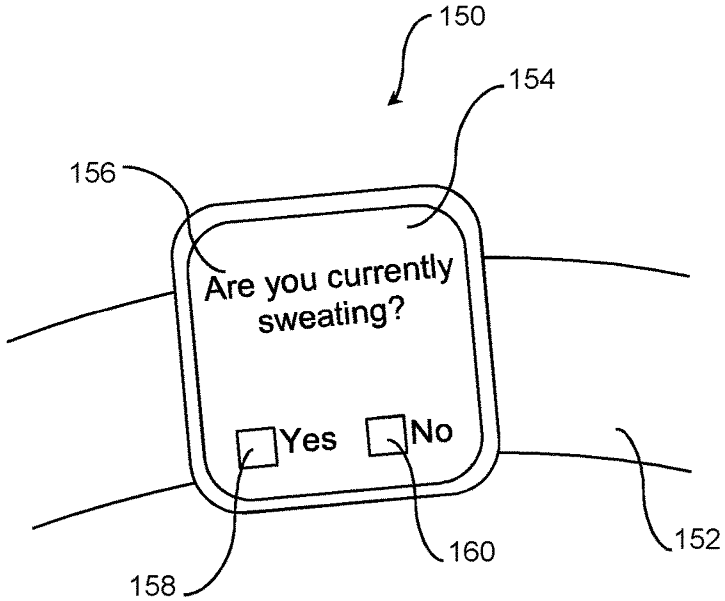
FIG. 18 is a schematic view of a wearable device.

FIG. 18 shows a wearable device 150 incorporating an apparatus for measuring the glucose level of a person. FIG. 18 shows a top view of the wearable device 150, on which a touch display 154 is provided, whereas the measurement body of the apparatus is provided on the bottom surface of the device (not shown in FIG. 18), such as to be in contact with the skin when the device 150 is worn around the user's wrist using a wrist band 152. All of the aforementioned components of the apparatus can be provided in the wearable device 150, including an excitation radiation source, a detection device for detecting the physical response of the measurement body to heat or pressure waves received from the skin upon absorption of the excitation radiation, and a control system (not shown). In the embodiment shown, on the touch display 154, a user is prompted to provide user-related input allowing for optimizing one or both of the analyte measuring procedure and the analysis carried out in the analyzing step. Such user related input may comprise characteristics or conditions of the person using the wearable device 150 for glucose measurement. For example, in the situation shown in FIG. 18, the user is asked to state whether he or she is currently sweating (see reference sign 156). The user is prompted to answer yes or no by ticking boxes 158 and 106, respectively, on the touch display 154. A state of sweating would be one example of a condition of the user. Further examples of the condition could be whether the person has a cold and/or a fever or whether the person is feeling cold, is currently on a diet, has recently drunken water or feels stressed. This information could also be inputted via a smartphone or another device which communicates with the wearable device 150, and can be inputted via a graphical user interface or via sound and a microphone in combination with speech recognition.

In addition to querying for a user's condition, the apparatus may further be configured to also query characteristics of a user. While a sharp distinction between characteristics and conditions of the user may be arguable, as understood herein, "conditions" refer to estates or properties that are expected to change e.g. within hours or at least a few days, whereas characteristics will only change on longer time scales and therefore do not have to be assessed as frequently as conditions. Examples of the characteristics would for example be the colour of the skin of the person, for example whether the person's skin is of light or dark colour, information related to the weight of the person, for example a body mass index, whether or not the person suffers from chronic diseases, and, if yes, which ones (for example, whether the person suffers from diabetes or whether the glucose measurement is done for general health or nutrition monitoring), and the age of the person.

The characteristics can be queried via the touch display 154 in the same manner, but will be queried less frequently than the conditions. The query for user-related information can e.g. be carried out by the apparatus (its control system) prior to step 70 in FIG. 7. At least some of the information about characteristics may also be acquired using sensors. For example, the color of the skin may be determined using a camera and a respective image analysis.

The user-related information can be used in addition to the information established in the material state analyzing procedure 76. That is to say, all of the selections and determinations made in steps 102, 104 and 106 based on the result of the material status analyzing procedure can be made based on both, the result of the material analyzing procedure and the user-related input received. However, in other cases, the user input could be used instead of the information established in the material state analyzing procedure.

In some embodiments, a protocol for carrying out the analyte measuring procedure may be generated or selected from a number of predetermined protocols based on the user-related conditions/characteristics received by user input. The different protocol selected or generated based on the conditions/characteristics of the user may e.g. differ with respect to one or more of

- a selection of analyte-characteristic-wavelengths used during said analyte measurement procedure, or relied on during said analysis,
- an absolute time or a relative time proportion of use of analyte-characteristic-wavelengths during said analyte measurement procedure, or a relative weight given to the wavelengths in the analysis,
- a selection of analyte-characteristic-wavelengths to be used simultaneously during said analyte measurement procedure, and a selection of one or more main frequencies of the modulation of said excitation radiation intensity to be used during said analyte measurement procedure The protocols may have been previously empirically determined to work particularly well for the given characteristics and/or conditions. These predetermined protocols could be used instead of the material status analyzing procedure described with reference to FIG. 7 or 8. However, in particularly preferred embodiments, these protocols may be used as a starting point and then be refined based on the results of the material status analyzing procedure of FIGS. 7 and 8.

Moreover, the user-related input can additionally or alternatively be used for adapting the analysis carried out in the analyzing step. In the embodiment shown, the control system comprises a memory storing various algorithms that translate the response signals into an estimate of a glucose concentration.

In preferred embodiments, in said memory various machine-learning based algorithms are stored, which have been trained with training data associated with different characteristics and conditions. Then, based on the user input, one of these machine-learning based algorithms can be selected that has been trained with characteristics/conditions which are the most similar to the characteristics and conditions received by user input. Instead of selecting among alternative algorithms for use in the analysis, it may also be possible to simply adjust certain parameters of the algorithms based on the characteristics or conditions.

Figure 19:
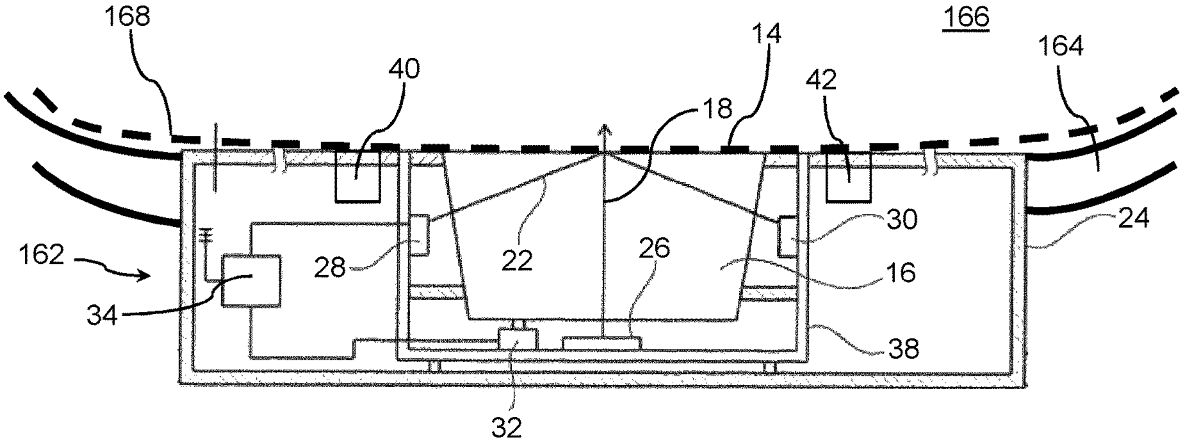
FIG. 19 is a schematic sectional view of an apparatus worn at the underside of a person's wrist.

FIG. 19 shows a sectional view of an apparatus 162 which is similar to that of FIG. 3. Same or similar components in FIG. 19 are denoted with the same reference signs as in FIG. 3 and are not described again. The apparatus 162 comprises a wrist band 164 for wearing the apparatus strapped to a wrist 166. In the embodiment shown, the apparatus 162 is a dedicated device to be worn at the underside of the wrist 166, where the surface of the skin of the underside of the wrist 166 is schematically illustrated by the dashed line 168. The inventors have found that the skin at the underside of the wrist 166 is a particularly suitable for precise glucose measurements. The same type of apparatus 162 might alternatively be integrated in a wearable device as shown under reference sign 150 in FIG. 18, in which case the measurement could be carried out at the upper side of the wrist 166, which is the normal position of the wearable device 150. It is however also possible to simply turn the wearable device 150 temporarily to the underside of the wrist 166 when carrying out the glucose measurement.

Shown in FIG. 19 is again a camera 32 which in the embodiment of FIG. 3, was used for recording fingerprints for user identification. However, in the embodiment shown in FIG. 19, the camera 32 is specifically configured for recording images of the region of the skin 168 where the excitation radiation 18 is to be radiated into the skin 168.

Figure 20:
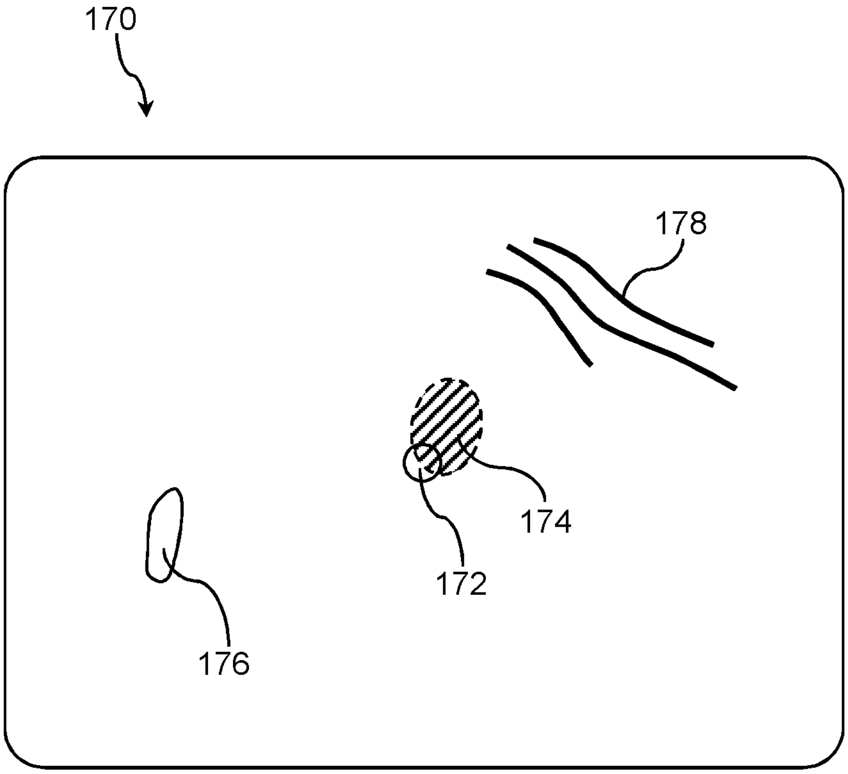
FIG. 20 is an image taken of the skin with the apparatus of FIG. 19.

FIG. 20 show s schematic representation of an image 170 taken through the measurement body 14 using the camera 32 of FIG. 19. In the image 170, the circle 172 denotes the location where the excitation light beam 18 will be radiated into the skin 168. This location 172 within the image 170 is known in advance (i.e. prior to irradiation with excitation light beam 18), e.g. due to a known relative position of the camera 32 and the excitation light source 26. This location 172 can also be determined in a calibration procedure.

Knowing this location 172 within the image 170, using a suitable algorithm it can then be determined, whether for the given position of the apparatus 162 relative to the skin 168, the excitation radiation will be radiated into the skin at a "suitable location". A "suitable location" would be a location where the quality of the skin is such that reliable measurement results can be expected. Reliable measurements are typically obtained where the skin is smooth, clean and free from wrinkles (schematically shown under reference sign 178), scars 176 or moles 174. From the image 170 shown in FIG. 20, an algorithm could determine that the radiation location 172 overlaps with the mole 174 discerned in the image 170, which means that for this relative positon of the apparatus 162 with respect to the skin 168, the excitation beam 18 would actually not be directed to a "suitable location".

This is determined using an image analysis algorithm, and in response to the determination, the user is prompted via an output interface to relocate apparatus 162 with respect to the skin 168. The user interface may again be a touch display. In addition or alternatively, the output interface may comprise an acoustic output device.

This way, it can be ensured that the measurement is carried out at a proper location of the skin 168, thereby eliminating one source of imprecise measurement results.

A further source of imprecise measurements is a lack of positional stability, i.e. if the apparatus 162 is moved with respect to the skin 168 during the measurement. In the embodiment shown, images of the skin are not only taken prior to carrying out the measurement, but also in regular intervals during the analyte measurement procedure. Consecutively recorded images of the skin are compared, and if the images deviate from each other, this is an indication that the apparatus 162 has moved. If it is determined that the apparatus 162 has moved, this can be an indication to terminate the analyte measurement procedure and start it anew.

In some cases, even if it has been determined that the apparatus 162 has moved relative to the skin 168, it may be advantageous to not terminate the analyte measurement procedure, but to possibly repeat portions of it, or extend the measurement time devoted for a given wavelength which is presumably affected by the change in position. Similarly, the relative movement of the apparatus 162 with respect to the skin 168 may lead to a situation in which the location 172 where the excitation light beam 18 impinges on the skin 168 is no longer a suitable location according to one of the criteria applied. In this case, too, it can be decided to terminate the measurement or to adapt the measurement protocol.

Note that the information with respect to suitable location of the excitation radiation and/or position stability can be exploited in a similar manner as in the "quality assessment" described above, except that the quality assessment described above was based on the response signal, not on camera images.

In particular, based on the detected positon stability, the measurement time devoted to one or more analyte-characteristic-wavelengths during the current analyte measurement procedure can be adjusted. In the alternative, the relative weight associated with the corresponding analyte-wavelength-specific measurement in the analysis may be adjusted, in a manner explained above with reference to the quality assessment. In addition or alternatively, based on the position stability monitored, the measurement can be terminated and started again.

It should be taken note that for the above mentioned applications of a camera generally any camera or imaging device may be used which is sensitive in the optical range of light, i.e. in the range that can be perceived by a human being, but it may also be advantageous to use an infrared camera or a kind of a camera which is sensitive in special ranges or segments of the optical, infrared or UV spectrum. The realization of the sensitivity range may be implemented e.g. by inserted filters.

In the embodiment shown, the apparatus is configured to inform the user if the measurement is terminated due to a relative movement between apparatus 162 (or its measurement body 16) and the skin 168. While the user does not have to actively do anything to restart the analyte measurement procedure, this will increase the users awareness and hence ensure a positional stability in the next attempt of the analyte measurement procedure. Preferably, this information is conveyed via an acoustic signal to the user.

While the present invention has been described in terms of specific embodiments, it is understood that variations and modifications will occur to those in the art, all of which are intended as aspects of the present invention. Accordingly, only such limitations as appear in the claims should be placed on the invention.

The invention claimed is:

1. A method of analyzing a material comprising at least one analyte, said method comprising an analyte measurement procedure, in which the material is brought in thermal contact or pressure transmitting contact with a measurement body, said thermal or pressure transmitting contact permitting heat or pressure waves generated by absorption of excitation radiation in the material to be transferred to said measurement body, excitation radiation is irradiated into the material to be absorbed therein, wherein the intensity of said excitation radiation is time-modulated, and wherein said excitation radiation comprises radiation of different analyte-characteristic-wavelengths that are irradiated one or both of simultaneously and sequentially, and a physical response of the measurement body, or of a component included therein, to heat or pressure waves received from said material upon absorption of said excitation radiation is detected using a detection device which generates a response signal based on said detected physical response, said response signal being indicative of a degree of absorption of excitation radiation, wherein the method further comprises an analyzing step, in which said analyzing is carried out based, at least in part, on said response signal, wherein during said analyte measurement procedure, a sequence of analyte-wavelength-specific measurements is carried out while maintaining said thermal or pressure transmitting contact between the material and the measurement body, wherein in each analyte-wavelength-specific measurement, excitation radiation with an analyte-characteristic-wavelength selected from a predetermined set of analyte-characteristic-wavelengths is irradiated and a corresponding response signal is obtained, and wherein at least some of said analyte-wavelength-specific measurements are interspersed with reference measurements, in which excitation radiation with a reference wavelength is irradiated and a corresponding response signal is obtained, wherein said reference wavelength is a wavelength different from any of said analyte-characteristic-wavelengths, and wherein said response signals obtained for the reference measurements are used for one or more of calibrating an excitation radiation source for generating said excitation radiation, calibrating said detection device, and adapting the analyte measurement procedure with respect to the absolute or relative duration of analyte-wavelength-specific measurements for a given analyte-characteristic-wavelength.

2. The method of claim 1, wherein between at least 25% of each pairs of successive analyte-wavelength-specific measurements, a reference measurement is carried out.

3. The method of claim 1, wherein said reference measurements are carried out at an average rate of at least once every 5 seconds.

4. The method of claim 1, wherein said material is human skin, and said analyte is glucose present in an interstitial fluid thereof.

5. The method of claim 1, wherein said detection device comprises a light source for generating a detection light beam travelling through at least a portion of said measurement body or a component included in said measurement body, said physical response of the measurement body to heat or pressure waves received from said material upon absorption of said excitation radiation is a local change in the refractive index of said measurement body or said component, and said detection device is configured for detecting one of a change in the light path or a change in the phase of detection beam due to said change in refractive index change in light path or phase of the detection beam.

6. The method of claim 5, wherein said measurement body is transparent for said detection light beam, said detection light beam is directed to be totally or partially reflected at a surface of said measurement body that is in thermal or pressure transmitting contact with said material, and wherein said detection device comprises a photodetector capable of detecting a degree of deflection of said detection light beam due to said local change in refractive index.

7. The method of claim 5, wherein said detection device comprises an interferometric device configured for assessing said change in phase of the detection beam and generating a response signal indicative of said change in phase.

8. The method of claim 1, wherein said measurement body or a component in said measurement body has electrical properties that change in response to a local change in temperature or a change in pressure associated therewith, and wherein said detection device comprises electrodes for capturing electrical signals representing said electrical properties.

9. The method of claim 1, wherein said excitation radiation is generated using an array of quantum cascade lasers, each having a dedicated wavelength.

10. The method of claim 1, wherein said excitation radiation is generated using at least one tunable quantum cascade laser.

11. The method of claim 1, wherein some or all of said excitation wavelengths are in a range of 6 μm to 13 μm.

12. A method of analyzing a material comprising at least one analyte, said method comprising an analyte measurement procedure, in which the material is brought in thermal contact or pressure transmitting contact with a measurement body, said thermal or pressure transmitting contact permitting heat or pressure waves generated by absorption of excitation radiation in the material to be transferred to said measurement body, excitation radiation is irradiated into the material to be absorbed therein, wherein the intensity of said excitation radiation is time-modulated, and wherein said excitation radiation comprises radiation of different analyte-characteristic-wavelengths that are irradiated one or both of simultaneously and sequentially, and a physical response of the measurement body, or of a component included therein, to heat or pressure waves received from said material upon absorption of said excitation radiation is detected using a detection device which generates a response signal based on said detected physical response, said response signal being indicative of a degree of absorption of excitation radiation, wherein the method further comprises an analyzing step, in which said analyzing is carried out based, at least in part, on said response signal, wherein during said analyte measurement procedure, a sequence of analyte-wavelength-specific measurements is carried out while maintaining said thermal or pressure transmitting contact between the material and the measurement body, wherein in each analyte-wavelength-specific measurement excitation radiation with an analyte-characteristic-wavelength selected from a predetermined set of analyte-characteristic-wavelengths is irradiated and a corresponding response signal is obtained, and wherein at least some of said analyte-wavelength-specific measurements are interspersed with reference measurements, in which excitation radiation with a reference wavelength is irradiated and a corresponding response signal is obtained, wherein said reference wavelength is a wavelength different from any of said analyte-characteristic-wavelengths, and wherein said response signals obtained for the reference measurements are used for adapting the analysis carried out in the analyzing step, wherein said step of adapting the analysis carried out in the analyzing step based on the response signal obtained for the reference measurements comprises normalizing results of at least some of the analyte-wavelength-specific measurements based at least in part on the results of one or both of a preceding or succeeding reference measurement.

13. An apparatus for analyzing a material comprising at least one analyte, said apparatus comprising a measurement body having a contact surface suitable to be brought in thermal contact or pressure transmitting contact with said material, said thermal or pressure transmitting contact permitting heat or pressure waves generated by absorption of excitation radiation in the material to be transferred to said measurement body, an excitation radiation source configured for irradiating excitation radiation into the material to be absorbed therein, a detection device for detecting a physical response of the measurement body, or of a component included therein, to heat or pressure waves received from said material upon absorption of said excitation radiation and for generating a response signal based on said detected physical response, said response signal being indicative of a degree of absorption of excitation radiation, and a control system, wherein said control system is configured to control the excitation radiation source to irradiate excitation radiation into the material to be absorbed therein, wherein the intensity of said excitation radiation is time-modulated, and wherein said excitation radiation comprises radiation of different analyte-characteristic-wavelengths that are irradiated one or both of simultaneously and sequentially, and control the detection device to detect said physical response and to generate response signals indicative of the degree of absorption of said excitation radiation, wherein said control system is further configured for controlling the apparatus to carry out a sequence of analyte-wavelength-specific measurements during said analyte measurement procedure while said thermal or pressure transmitting contact between the material and the measurement body is maintained, wherein in each analyte-wavelength-specific measurement, excitation radiation with an analyte-characteristic-wavelength selected from a predetermined set of analyte-characteristic-wavelengths is irradiated and a corresponding response signal is obtained, and wherein the control system is further configured for interspersing at least some of said analyte-wavelength-specific measurements with reference measurements, in which excitation radiation with a reference wavelength is irradiated and a corresponding response signal is obtained, wherein said reference wavelength is a wavelength different from any of said analyte-characteristic-wavelengths, and wherein said control system is configured for using response signals obtained for the reference measurements for one or more of calibrating an excitation radiation source for generating said excitation radiation, calibrating said detection device, and adapting the analyte measurement procedure with respect to the absolute or relative duration of analyte-wavelength-specific measurements for a given analyte-characteristic-wavelength.

14. The apparatus of claim 13, wherein between at least 25% of each pairs of successive analyte-wavelength-specific measurements, a reference measurement is carried out.

15. The apparatus of claim 13, wherein said control system is configured to control the apparatus such that said reference measurements are carried out at an average rate of at least once every 5 seconds.

16. An apparatus for analyzing a material comprising at least one analyte, said apparatus comprising a measurement body having a contact surface suitable to be brought in thermal contact or pressure transmitting contact with said material, said thermal or pressure transmitting contact permitting heat or pressure waves generated by absorption of excitation radiation in the material to be transferred to said measurement body, an excitation radiation source configured for irradiating excitation radiation into the material to be absorbed therein, a detection device for detecting a physical response of the measurement body, or of a component included therein, to heat or pressure waves received from said material upon absorption of said excitation radiation and for generating a response signal based on said detected physical response, said response signal being indicative of a degree of absorption of excitation radiation, and a control system, wherein said control system is configured to control the excitation radiation source to irradiate excitation radiation into the material to be absorbed therein, wherein the intensity of said excitation radiation is time-modulated, and wherein said excitation radiation comprises radiation of different analyte-characteristic-wavelengths that are irradiated one or both of simultaneously and sequentially, and control the detection device to detect said physical response and to generate response signals indicative of the degree of absorption of said excitation radiation, wherein said control system is further configured for controlling the apparatus to carry out a sequence of analyte-wavelength-specific measurements during said analyte measurement procedure while said thermal or pressure transmitting contact between the material and the measurement body is maintained, wherein in each analyte-wavelength-specific measurement, excitation radiation with an analyte-characteristic-wavelength selected from a predetermined set of analyte-characteristic-wavelengths is irradiated and a corresponding response signal is obtained, and wherein the control system is further configured for interspersing at least some of said analyte-wavelength-specific measurements with reference measurements, in which excitation radiation with a reference wavelength is irradiated and corresponding response signal is obtained, wherein said reference wavelength is a wavelength different from any of said analyte-characteristic wavelengths, and wherein said control system is configured for using response signals obtained for the reference measurements for adapting an analysis, wherein the analysis based on the response signal obtained for the reference measurements comprises normalizing results of at least some of the analyte-wavelength-specific measurements based at least in part on the results of one or both of a preceding or succeeding reference measurement.

* * * * *